(12) United States Patent
Shan et al.

(10) Patent No.: US 6,930,219 B2
(45) Date of Patent: Aug. 16, 2005

(54) MESOPOROUS MATERIAL WITH ACTIVE METALS

(75) Inventors: Zhiping Shan, Bloomfield, NJ (US); Jacobus Cornelius Jansen, Delft (NL); Chuen Y. Yeh, Edison, NJ (US); Philip J. Angevine, Woodbury, NJ (US); Thomas Maschmeyer, Wilhelminalaan (NL); Mohamed S. Hamdy, Delft (NL)

(73) Assignee: ABB Lummus Global Inc., Bloomfield, NJ (US)

( * ) Notice: Subject to any disclaimer, the term of this patent is extended or adjusted under 35 U.S.C. 154(b) by 257 days.

(21) Appl. No.: 10/313,720

(22) Filed: Dec. 6, 2002

(65) Prior Publication Data

US 2003/0188991 A1 Oct. 9, 2003

Related U.S. Application Data

(63) Continuation-in-part of application No. 09/995,227, filed on Nov. 27, 2001, now Pat. No. 6,762,143, which is a continuation-in-part of application No. 09/390,276, filed on Sep. 7, 1999, now Pat. No. 6,358,486.

(51) Int. Cl.[7] .............................. C07C 2/12; C07C 2/66; C07C 5/03; C07C 5/10; C07C 5/22; C07C 5/32; C07C 5/333; C07C 249/00; C07C 37/00; C10G 11/02; C10G 25/00; C10G 73/02; A61K 38/00; C07D 301/00

(52) U.S. Cl. ....................... 585/533; 585/467; 585/722; 585/481; 585/739; 585/666; 585/275; 585/444; 585/660; 585/661; 585/820; 208/210; 208/89; 208/118; 208/143; 208/254 H; 208/213; 208/27; 568/771; 530/345; 564/253; 549/540

(58) Field of Search ................................ 585/533, 467, 585/722, 481, 739, 666, 275, 444, 660, 661, 820; 530/345; 568/771; 208/210, 84, 118, 143, 254 H, 213, 27; 564/253; 549/540

(56) References Cited

U.S. PATENT DOCUMENTS

| | | |
|---|---|---|
| 3,959,174 A | 5/1976 | Winyall et al. |
| 5,057,296 A | 10/1991 | Beck |
| 5,098,684 A | 3/1992 | Kresge et al. |
| 5,102,643 A | 4/1992 | Kresge et al. |
| 5,108,725 A | 4/1992 | Beck et al. |
| 5,110,572 A | 5/1992 | Calabro et al. |
| 5,191,134 A | 3/1993 | Le |
| 5,191,148 A | 3/1993 | Degnan et al. |
| 5,264,203 A | 11/1993 | Beck et al. |

(Continued)

OTHER PUBLICATIONS

Shan et al., *Synthesis, characterization and catalytic testing of a 3–D mesoporous titanosilica, Ti–TUD–1*, ELSEVIER, (2001) pp. 181–187.

Shan et al., *One–Step Synthesis of a Highly Active, Mesoporous, Titanium–Containing Silica by Using Bifunctional Templating*, Chem. Eur. J. 2001, 7 No. 7, pp. 1437–1443.

*Primary Examiner*—Thuan D Dang
(74) *Attorney, Agent, or Firm*—Dilworth & Barrese, LLP

(57) ABSTRACT

A process for treating organic compounds includes providing a composition which includes a substantially mesoporous structure of silica containing at least 97% by volume of pores having a pore size ranging from about 15 Å to about 30 Å and having a micropore volume of at least about 0.01 cc/g, wherein the mesoporous structure has incorporated therewith at least about 0.02% by weight of at least one catalytically and/or chemically active heteroatom selected from the group consisting of Al, Ti, V, Cr, Zn, Fe, Sn, Mo, Ga, Ni, Co, In, Zr, Mn, Cu, Mg, Pd, Pt and W, and the catalyst has an X-ray diffraction pattern with one peak at 0.3° to about 3.5° at 2θ. The catalyst is contacted with an organic feed under reaction conditions wherein the treating process is selected from alkylation, acylation, oligomerization, selective oxidation, hydrotreating, isomerization, demetalation, catalytic dewaxing, hydroxylation, hydrogenation, ammoximation, isomerization, dehydrogenation, cracking and adsorption.

34 Claims, 22 Drawing Sheets

U.S. PATENT DOCUMENTS

| | | |
|---|---|---|
| 5,374,747 A | 12/1994 | Saxton et al. |
| 5,622,684 A | 4/1997 | Pinnavaia et al. |
| 5,672,556 A | 9/1997 | Pinnavaia et al. |
| 5,707,917 A | 1/1998 | Geus et al. |
| 5,795,555 A | 8/1998 | Alive et al. |
| 5,811,599 A | 9/1998 | Alive et al. |
| 5,849,258 A | 12/1998 | Lujano et al. |
| 5,948,683 A | 9/1999 | Koermer et al. |
| 6,133,186 A | 10/2000 | Gosselink et al. |
| 6,358,486 B1 | 3/2002 | Shan et al. |

MESOPOROUS MATERIAL WITH ACTIVE METALS

CROSS-REFERENCE TO RELATED APPLICATIONS

The present application is a continuation in part of U.S. application Ser. No. 09/995,227 filed Nov. 27, 2001 now U.S. Pat. No. 6,762,143 and incorporated by reference herein, which is a continuation in part of U.S. application Ser. No. 09/390,276 filed Sep. 7, 1999, now issued as U.S. Pat. No. 6,358,486 B1, to which priority is claimed.

BACKGROUND

1. Field of the Invention

The present invention relates to a mesoporous material, particularly a catalytic material, and use of the mesoporous material for the conversion of organic compounds, particularly hydrocarbons.

2. Background of the Prior Art

Most of today's hydrocarbon processing technologies are based on zeolite catalysts. Zeolite catalysts are well known in the art and possess well-arranged pore systems with uniform pore sizes. However, these materials tend to possess either only micropores or only mesopores. Micropores are defined as pores having a diameter less than about 2 nm. Mesopores are defined as pores having a diameter ranging from about 2 nm to about 50 nm.

Because such hydrocarbon processing reactions are mass-transfer limited, a catalyst with an ideal pore size will facilitate transport of the reactants to active catalyst sites and transport the products out of the catalyst.

There is yet need for an improved material having functionalized sites within a porous framework for processes directed to the catalytic conversion and/or adsorption of hydrocarbons and other organic compounds.

SUMMARY OF THE INVENTION

A process for treating organic compounds is provided herein. The process comprises: (a) providing a composition which includes a substantially mesoporous structure of silica containing at least 97% by volume of pores having a pore size ranging from about 15 Å to about 30 Å and having a micropore volume of at least about 0.01 cc/g, wherein the mesoporous structure has incorporated therewith at least about 0.02% by weight of catalytically and/or chemically active heteroatoms selected from the group consisting of Al, Ti, V, Cr, Zn, Fe, Sn, Mo, Ga, Ni, Co, In, Zr, Mn, Cu, Mg, Pd, Pt and W, and wherein said catalyst has an X-ray diffraction pattern with one peak at 0.3° to about 3.5° at 2 θ; and, (b) contacting an organic feed under reaction conditions with said catalyst wherein the treating process is selected from the group consisting of alkylation, acylation, oligomerization, selective oxidation, hydrotreating, isomerization, demetalation, catalytic dewaxing, hydroxylation, hydrogenation, ammoximation, isomerization, dehydrogenation, cracking and adsorption.

One aspect of this invention deals with an improved catalytic process for the demetalation and desulfurization of petroleum oils, preferably those residual fractions with undesirably high metals and/or sulfur and/or nitrogen contents and/or Conradson Carbon Residue (CCR). More particularly, this invention relates to a hydrotreating process for reducing high metals, sulfur and nitrogen contents and CCR of petroleum oils, again preferably those containing residual hydrocarbon components.

Residual petroleum oil fractions are produced by atmospheric or vacuum distillation of crude petroleum; they generally contain high amounts of metals, sulfur, nitrogen and CCR content. This comes about because practically all of the metals and CCR present in the original crude remain in the residual fraction, and a disproportionate amount of sulfur and nitrogen in the original crude oil also remains in that fraction. Principal metal contaminants are nickel and vanadium, with iron and small amounts of copper also sometimes present.

The high metals, sulfur, nitrogen, and CCR content of the residual fractions generally limit their effective use as charge stocks for subsequent catalyst processing such as catalytic cracking and hydrocracking. The metal contaminants deposit on the special catalysts for these cracking processes and cause the premature aging of the catalyst and/or unwanted side reactions such as cracking to coke, dry gas and hydrogen. During the FCC process, much of the sulfur ends up in the FCC catalyst's coke, which is burned during regeneration, resulting in substantial SOx emissions. Another major fate of the residua's sulfur is in the final cracked products, such as gasoline and light cycle oil (a blending component for diesel fuel and home heating fuel). Some of the nitrogen contributes to NOx emissions, and some nitrogen (the basic nitrogen compounds) becomes bound to the active sites of the FCC catalyst and renders it ineffective. CCR, a measure of a molecule's tendency to coke rather than crack and/or distill, is also an undesirable property for charge streams processed by catalytic cracking. Under the high temperature employed in catalytic cracking, molecules high in CCR thermally and/or catalytically degrade to coke, light gases, and hydrogen. Catalytic cracking is generally done utilizing hydrocarbon charge stocks lighter than residual fractions, which generally have an API gravity less than 20. The most common, cracking charge stocks are coker and/or crude unit gas oils, vacuum tower overheads, etc., the feedstock having an API gravity from about 15 to about 45. Since these cracking charge stocks are distillates, they do not contain significant proportions of the large molecules in which the metals are concentrated. Such cracking is commonly carried out in a reactor operated at a temperature of about 425 to 800° C., a pressure of about 1 to 5 atmospheres, and a space velocity of about 1 to 1000 WHSV.

Metals and sulfur contaminants would present similar problems in hydrocracking operations that are typically carried out on charge stocks even lighter than those charged to a cracking unit. Typical hydrocracking reactor conditions consist of a temperature of 200 to 550° C. and a pressure of 700 to 20,000 kPa.

It is evident that there is considerable need for an efficient method to reduce the metals and/or sulfur and/or nitrogen and/or CCR content of hydrocarbons, and particularly of residual petroleum fractions. While the technology to accomplish this for distillate fractions has been advanced considerably, attempts to apply this technology to residual fractions generally fail due to very rapid deactivation of the catalyst, primarily by metals contaminants and coke deposition.

BRIEF DESCRIPTION OF THE DRAWINGS

Various embodiments are described below with reference to the drawings wherein.

DETAILED DESCRIPTION OF PREFERRED EMBODIMENT(S)

Figure 1:
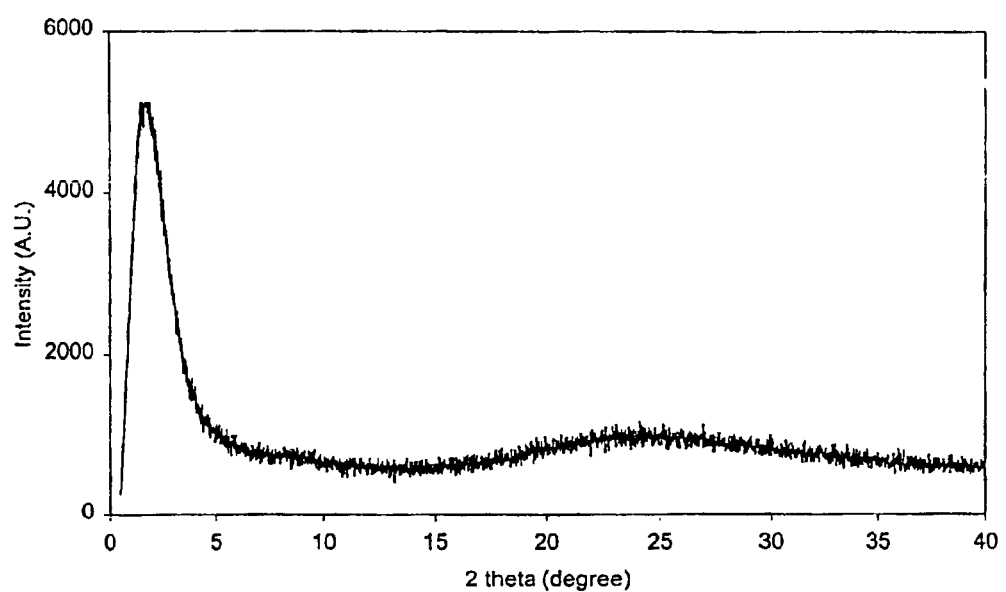
FIG. 1 is an X-ray diffraction pattern ("XRD") of the mesoporous material of Example 1.

The catalyst of the present invention includes a three-dimensional, stable, porous silica, which is substantially mesoporous in structure. The silica possesses a non-crystalline, but regularized (pseudo-crystalline) structure. Mesoporous materials are described in U.S. Pat. No. 6,358,486 B1, which is herein incorporated by reference in its entirety.

The amorphous silica material of the present invention generally contains both mesopores and micropores. Micropores are defined as pores having a diameter of less than about 2 nm. Mesopores are defined as pores having a diameter of from about 2 nm to about 50 nm. The inorganic oxide material of the present invention has a volume percentage of mesopores of at least about 97% and preferably at least about 98%.

A method for making a preferred porous silica-containing catalyst support is described in U.S. Pat. No. 6,358,486 B1. The average mesopore size of the preferred catalyst as determined from $N_2$-porosimetry ranges from about 2 nm to about 25 nm.

The catalyst includes, and is functionalized with, one or more catalytically active metal heteroatoms incorporated into the porous silicate structure. The catalytically active metal heteroatom (i.e., non-silicon atom) can be selected from Groups IB, IIB, IIIB, IVB, VB, VIB, VIIB, VIII, IVA, and IIIA of the Periodic Table of the Elements. Suitable metal heteroatoms include aluminum (Al), titanium (Ti), vanadium (V), chromium (Cr), zinc (Zn), iron (Fe), tin (Sn), molybdenum (Mo), gallium (Ga), nickel (Ni), cobalt (Co), indium (In), zirconium (Zr), manganese (Mn), copper (Cu), magnesium (Mg), palladium (Pd), platinum (Pt) and tungsten (W), for example. The incorporated heteroatoms can be isolated and/or distributed as clusters in the porous matrix. They can be in an atomic form or molecular form (e.g., as oxide). The heteroatom content of the catalyst is at least about 0.02% by weight of the catalyst. The atomic ratio of the heteroatoms to silicon atoms in the catalyst can be varied up to about 0.9, preferably from about 0.0001 to about 0.5.

The composition of the present invention has a characteristic X-ray diffraction pattern ("XRD") which shows at least one peak at 0.3° to 3.5° at 2 θ, which corresponds to a basal spacing between 25 Å and 440 Å. Nitrogen adsorption tests reveal a tunable pore size ranging from about 15 Å (1.5 nm) to about 300 Å (30 nm), and a surface area ranging from about 300 $m^2/g$ to about 1,250 $m^2/g$, and a pore volume of from about 0.3 cc/g to about 2.5 cc/g.

The composition of the present invention has a three-dimensional, randomly connected mesopore system, which facilitates mass-transfer of reactants and products, and avoids pore blockage.

Generally, the mesoporous silica material of the present invention is prepared from a synthesis mixture containing at least one silica source, at least one heteroatom source, and at least one pore-forming organic templating agent.

In a first stage of the method for making the catalyst of the invention, the silica source, heteroatom source, and organic templating agent(s) are combined in aqueous solution to form a synthesis mixture (usually a gel).

In an intermediate stage of the method, the volatile components of the synthesis mixture (e.g., water, alcohol) are removed by conventional means such as drying with or without forced air flow. The drying can be conducted, for example, at 40° C. to about 130° C. for up to about 72 hours, more preferably from about 60° C. to about 120° C. for 6 to 36 hours.

In a final stage the organic templating agent(s) are removed by conventional means such as calcining and extraction. Typically, the calcining is performed at a temperature of from about 450° C. to about 900° C. with an oxygen-containing gas (e.g., air) for 2 to 20 hours, preferably at 540° C. to about 700° C. for about 4 to 15 hours. The extraction can be done using organic solvents at a temperature of from about 30° C. to about 100° C., depending upon the solvent used. Some alcohols with low or no toxicity are preferable as solvents.

Optionally, the method can include aging the synthesis mixture at 10° C. for up to 24 hours before removing the volatile components of the synthesis mixture.

Optionally, the synthesis mixture can be heated in an autoclave at a temperature of from about 100° C. to about 220° C. for up to about 10 days, preferably at a temperature of from about 120° C. to about 200° C. for up to 96 hours, before removing the pore forming agent. The heating step in the autoclave can tune the mesoporosity to meet specific requirements. During the heating, inorganic species such as silicon and aluminum will coalesce to form an inorganic framework, while the pore forming agent, forms aggregates to shape the inorganic framework. The size distribution of the aggregates determines the mesopore size distribution. However, the aggregate size mainly depends on the nature of the pore forming agent, the temperature of heating and the length of the heating time. So for a certain pore-forming agent, the mesoporosity of the final material can be tuned by manipulating the temperature and the heating time.

More particularly, in the first stage, the silica source, or silica precursor, can be a silicon compound containing some organic groups. Such compounds can be alkoxides, e.g., tetraethyl orthosilicate ("TEOS"), and silatranes, e.g., triethanolamine-substituted silatranes. The silica source can alternatively be inorganic, such as anhydrous or hydrous silica gels or silica hydrogels. The silica source also can be geothermal silica, but to facilitate reactivity, is preferably not a crystalline source.

The organic templating agent preferably contains hydroxyl (—OH) groups that form hydrogen bonds with the inorganic species (i.e., silica and heteroatom). They may have atoms with a pair of electrons that can bond with the silicon or heteroatoms. Such organic templating agents include glycols (e.g., propylene glycol, glycerol, diethylene glycol, triethylene glycol, tetraethylene glycol), alkanolamines (e.g., triethanolamine ["TEA"], triisopropanolamine), diethylglycol dibenzoate, triethylene pentamine, starch, and sulfolane. The organic templating agent should have a boiling point above 150° C., preferably above about 180° C.

The heteroatom source can be with or without organic groups and is typically added in the form of a solution. For example, in the case of aluminum, the source can be aluminum alkoxide (e.g., aluminum isopropoxide), alumina, aluminum hydroxide, aluminum nitrate, aluminum sulfate, or aluminum chloride.

The synthesis mixture can also include alkali or acid to adjust the pH of the mixture. Alkalis typically include organic alkali such as tetraethylammonium hydroxide ("TEAOH") and other tetraalkylammonium hydroxides, urea, and the like, or inorganic alkali such as ammonium hydroxide, sodium hydroxide, sodium carbonate, and the like.

The solvents, reaction conditions, the order of adding and mixing components and the pH can depend upon the heteroatom and should be selected to avoid premature separation (e.g., precipitation) of the heteroatom. Premature separation can result in failure of the heteroatom to be incorporated into the silica structure.

The composition of the invention can be applied as catalysts, co-catalysts (a part of catalysts), catalyst supports, adsorbents and molecular sieves. Depending on the functionality of the incorporated heteroatoms, the composition can have weak, medium and strong acidity, consequently it can catalyze cracking, isomerization, alkylation, acylation, oligomerization/polymerization, dehydration of organic compounds and desulfurization. The composition can also have redox properties, which can catalyze epoxidation of alkenes (e.g., cyclohexene, octene, ethylene, or propylene), selective oxidation of alkanes (e.g. cyclododecane, cyclohexane), alcohols and amines, hydroxylation of aromatics,and ammoximation of ketones. The composition can be used as co-catalysts or catalyst supports. For instance, addition of noble metals, e.g. Pd and/or Pt/to this composition offers functionality of hydrocracking, hydrogenation, dehydrogenation, and desulfurization. This composition can also contain all types of zeolites and zeolite-like structures, together with all possible heteroatoms mentioned above.

A typical example of the composition of the invention, which offers acidity, is the one containing aluminum and/or gallium. A group of industrially important reactions is alkylation, which conventionally uses corrosive Lewis acids such as $AlCl_3$ and HF and generates large amount of wastes. The composition of this invention is environmental friendly and can replace the conventional catalysts. It can catalyze alkane or aromatic alkylation (including Friedel-Crafts alkylation) using olefins, alkyl halides or alcohols as alkylation agents. The aromatic compounds mainly include benzene, naphthalene, phenanthrene and their derivatives, such as toluene, xylene, isopropylnaphthalene, di-phenyl oxide, or 2,4-di-t-butylphenol. The olefin alkylation agents mainly include alpha-olefins, preferably those with a carbon number more than two, preferably more than four. Suitable olefins include e.g., ethylene, propylene, and 1-hexadecene. Alcohol alkylation agents mainly include methanol, ethanol, isopropanol, benzyl alcohol, and cinnamyl alcohol. The alkylation reaction can be carried out at a temperature of from about 80° C. to about 400° C., under a pressure between 1 and 50 bars, preferably from about 90° C. to about 300° C. and between 1 and 30 bars.

Oligomerization and polymerization of olefins can produce fractions for gasoline, jet fuel, diesel fuel and lubricating base oil. The catalyst composition of the invention, especially those containing aluminum, chromium, gallium or iron heteroatoms, can be used as catalysts for oligomerization of olefins such as alpha-olefins with a carbon number larger greater than three. Reaction conditions, depending on the specific feedstocks and desired products, include a temperature ranging from about 25° C. to about 300° C., and a pressure ranging from atmospheric pressure to about 70 bars.

The catalyst composition of the invention can be used for the selective oxidation of organic compounds. Particularly preferred are those catalyst compositions containing one or more heteroatoms selected from transition metals including, for example, copper, zinc, iron, titanium, chromium, vanadium, molybdenum and tin. For instance, the composition containing titanium, zinc, chromium, iron and manganese can catalyze epoxidation of olefins including aromatics such as phenanthrene, anthracene and trans-stilbene. The oxidants used in this type of reaction include organic or inorganic peroxides, nitrogen oxides, oxygen and any gas mixture containing oxygen. The composition containing copper and zinc is particularly preferred for catalyzing the selective oxidation of alcohols to corresponding aldehydes. Hydroxylation of phenol and 1-naphthol can be accomplished using the catalyst composition containing tin, iron, copper, cobalt and vanadium.

In the prior art, acylation of aromatics was conventionally performed using Lewis acids, such as $AlCl_3$, $FeCl_3$, $H_2SO_4$, etc. which generated a huge amount of wastes. In contrast, the composition of the present invention, especially embodiments that contain aluminum, iron, gallium, indium, etc., replaces the Lewis acids. Acylation agents mainly include acyl halide, carboxyl acid anhydride. The aromatic compounds mainly include benzene, naphthalene, phenanthrene and their derivatives. Acylation can be carried out at a temperature from about 40° C. to about 300° C., under a pressure of from about 0.5 bar to about 20 bars, preferably from about 60° C. to about 250° C., and a pressure of from about 1 to 15 bars.

When incorporated as heteroatoms in the mesoporous silica of the invention, transition metals such as cobalt, nickel, molybdenum, tungsten, or combinations thereof, or noble metals such as platinum, palladium or combinations thereof, provide catalysts particularly suitable for hydrotreating process such as (1) hydrogenation of aromatics in gasoline, jet fuel, diesel fuel and lubricating oil; (2) hydrocracking of heavy fractions such as vacuum gas oil, residuum fractions and liquids derived from coal (coal oil); (3) CCR reduction, denitrogenation, desulfurization, and demetalation of hydrocarbons, including the above-mentioned fractions. Demetalation is particularly useful for the removal of iron, nickel, vanadium, and arsenic. Hydrotreating reaction conditions typically include a reaction temperature ranging from about 40° C. to about 400° C., preferably from about 60° C. to about 350° C., and a pressure ranging from atmospheric pressure to about 300 bars.

Isomerization of hydrocarbons (e.g. n-butane, n-pentane, t-butene and xylene) can be catalyzed by using the catalyst of the invention. Preferred catalyst compositions for isomerization contain zirconium, tungsten, gallium, iron, titanium and aluminum as heteroatoms.

Dehydrogenation of saturated hydrocarbons to unsaturated hydrocarbons can be catalyzed using the composition containing mainly vanadium, iron, gallium, cobalt and chromium. The saturated hydrocarbon can be, for example, propane, isobutane and ethylbenzene. The gas hourly space velocity (GHSV) normally ranges from 100 to 2000 $hr^{-1}$, preferably from 500 to 1000 $hr^{-1}$. The operating pressure normally ranges from about 7 kPa to about 600 kPa, preferably from about 7 kPa to about 400 kPa. The reaction temperature typically ranges from about 350° C. to about 650° C., preferably from about 450° C. to about 600° C.

Hydrocarbon cracking can advantageously be carried out using the inventive catalyst composition containing nickel, tungsten, cobalt, molybdenum, aluminum and/or gallium. Moreover, the catalyst composition of the invention can be used alone or together with zeolites. The hydrocarbon can be feedstock for fluid catalytic cracking, hydrocracking, etc. The catalyst composition can also catalyze the cracking of waste polymers to recover useful fractions of desirable chemicals.

The composition can be used as a catalyst for Fischer-Tropsch process. The process involves contacting a feed stream comprising hydrogen and carbon monoxide with the catalyst in a reaction zone maintained at conversion-promoting conditions effective to produce an effluent stream comprising hydrocarbons. The gas hourly space velocity (GHSV) may range from about 100 volumes/hour/volume catalyst ($hr^{-1}$) to about 10,000 $hr^{-1}$, preferably from about 300 $hr^{-1}$ to about 2,000 $hr^{-1}$. The reaction temperature is typically in the range from about 160° C. to about 300° C., preferably from about 190° C. to about 260° C. The reaction pressure is typically in the range of about 5 bar to about 60 bar, preferably from 8 bar to about 30 bar.

The composition can be used to effectively and selectively adsorb particular compounds. Due to its tunable pores and functionalized pore wall, it allows various compounds to enter the pores and interact with functional heteroatom groups on or in the wall. For instance, the incorporated heteroatoms can have high but unsaturated coordination numbers, which enables the heteroatoms to form coordination bonds with oxygen-containing, nitrogen-containing, and sulfur-containing compounds, thereby effectively removing these compounds from streams. It can also be a base-acid interaction. For example, the composition containing aluminum can remove toxic compounds such as cyanuric acid and p-chlorophenol from streams. As such, the composition can be used as adsorbents and molecular sieves.

The invention disclosure presents a new type of mesoporous or meso-microporous silicate containing heteroatoms, having a randomly connected three-dimensional pore structure with tunable pore sizes. It offers a new, cost-effective process to synthesize the mesoporous silicate without any surfactant involved. It provides new diverse catalytic materials. And it provides the processes to apply the composition in catalysis and separation.

Various features of the invention are illustrated by the Examples given below. X-ray powder diffraction patterns (XRD) of the resulting materials were recorded using CuK, radiation on a Philips PW 1840 diffractometer equipped with a graphite monochromator. The samples were scanned in the range of 0.5–40° 2 θ with steps of 0.02°. Transmission electron microscopy (TEM) was performed using a Philips CM30T electron microscope with a LaB6 filament as the source of electrons operated at 300 kV. Nitrogen sorption isotherms,were measured on the Quantachrome Autosorb-6B at 77 K. Mesoporosity was calculated using the Barrett, Joyner and Halenda (BHJ) method. All composition parts are by weight unless indicated otherwise.

EXAMPLE 1

This example shows how to incorporate aluminum into silica without heating in an autoclave before calcination.

First, 1 part aluminum isopropoxide ($Al(iso-OC_3H_6)_3$) was added into 26 parts of an aqueous solution of tetraethylammonium hydroxide (TEAOH, 35%) while stirring. After dissolution, 38 parts of triethanolamine (TEA) together with 8 parts of water were added into the above solution under stirring. Then, 26 parts of tetraethyl orthosilicate (TEOS) were added under vigorous stirring. A clear solution was obtained. The stirring was continued for 1 hour, and then the synthesis mixture was aged at room temperature overnight and dried at 98° C. in air for 24 hours. Finally, the synthesis mixture was calcined at 570° C. for 10 hours in air with a ramp rate of 1° C./min.

Figure 2:
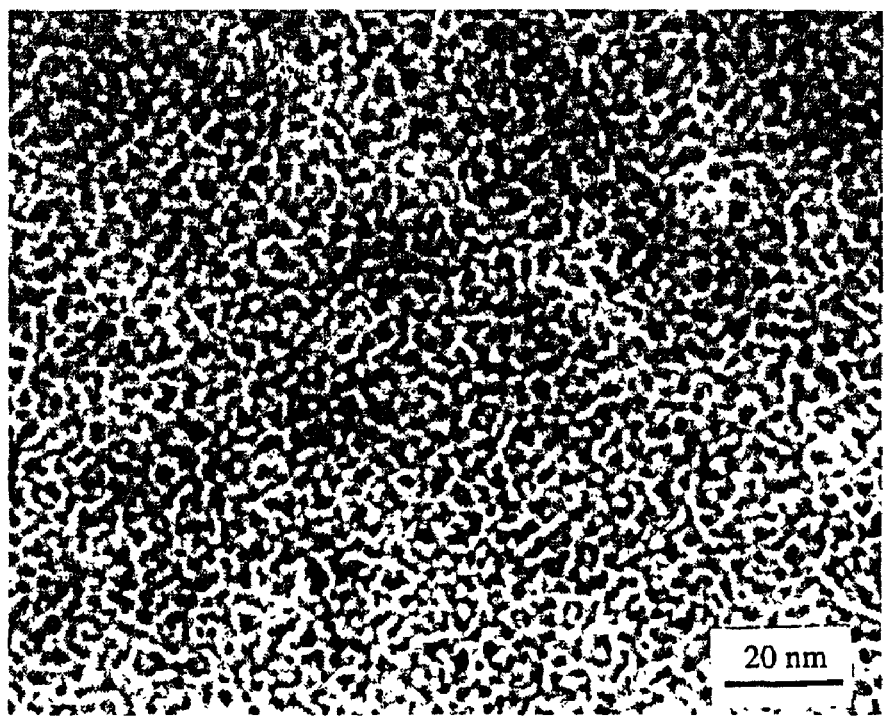
FIG. 2 is a transmission electron microscopy ("TEM") image of the mesoporous material of Example 1.
Figure 3:
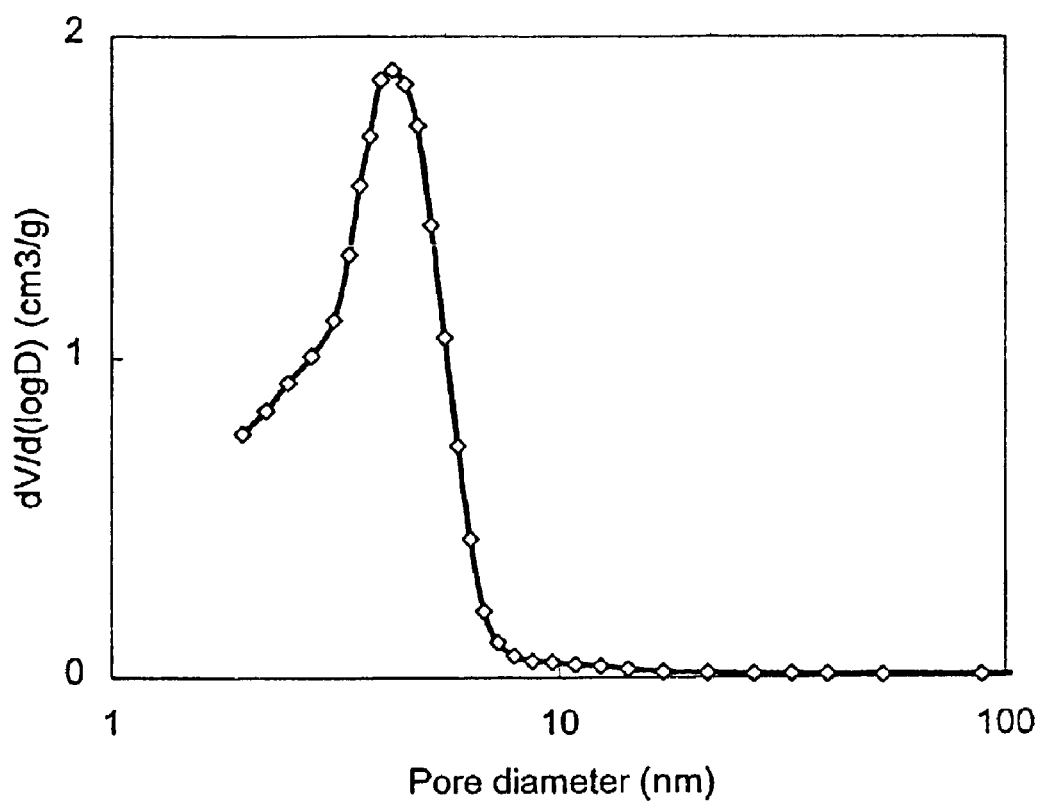
FIG. 3 is a graph illustrating the pore size distribution of the mesoporous material of Example 1.

FIG. 1 shows its XRD pattern with an intensive reflection at about 1.1° in 2 θ, indicating the characteristic of a mesoporous material. In addition, the absence of resolved peaks for alumina implies that no bulky alumina phase formed. FIG. 2 presents an image of transmission electron microscopy (TEM), showing a randomly connected mesoporous structure. Elemental analysis showed it to have a Si/Al ratio of about 24.8, which is consistent with the ratio of the initial synthesis mixture of 25. Nitrogen adsorption revealed a surface area of 983 $m^2/g$, a total pore volume of 1.27 $cm^3/g$ and a narrow mesopore distribution centered at 4.2 nm, shown in FIG. 3.

EXAMPLE 2

This example demonstrates the incorporation of heteroatoms with heating in an autoclave before calcination. 3.3 Parts of aluminum isopropoxide were added into a bottle with 42 parts of TEOS and stirred for an hour. A mixture of 7.6 parts of TEA and 25.8 parts of water were added into the mixture of TEOS and $Al(iso-OC_3H_6)_3$ under stirring. After 2 hours stirring, 21 parts of TEAOH were drop-wise added into the above mixture and a thick gel formed. The gel was dried in an oven at 98° C. for 22 hours and then transferred into an autoclave at 190° C. for 16 hours. Finally the gel was calcined at 600° C. for 10 hours in air.

Figure 4:
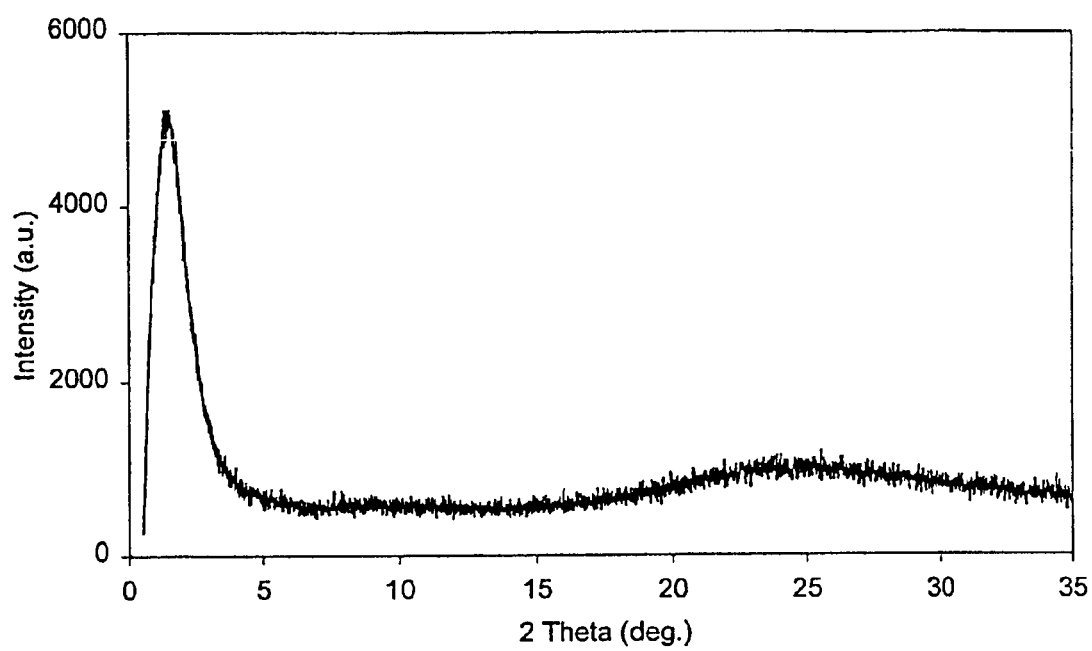
FIG. 4 is an XRD pattern of the mesoporous material of Example 2.

FIG. 4 shows its XRD pattern with an intensive reflection at a low angle in 2 θ, indicating the characteristic of mesoporous material. Elemental analysis showed its Si/Al ratio of about 24.5, consistent with the ratio of initial synthesis mixture was 25. Nitrogen adsorption revealed a surface area of 799 m²/g, a total pore volume of 1.24 cm³/g and a narrow mesopore distribution centered at 4.5 nm.

EXAMPLE 3A

This demonstrates the incorporation of aluminum and its stability of the composition. 3 Parts of aluminum isopropoxide were added into a bottle with 38.8 parts of TEOS and stirred for 1.5 hours. A mixture of 23 parts of TEA and 21 parts of water was added into the above mixture under stirring. After 2 hours stirring, 23 parts of TEAOH were drop-wise added into the above mixture and after 0.5 hours stirring it turned into a clear solution. The solution was dried in an oven at 100° C. for 4 days and then transferred into an autoclave at 190° C. for 7.5 days. Finally it was calcined at 600° C. for 10 hours with a ramp rate of 1° C./min in air.

Figure 5:
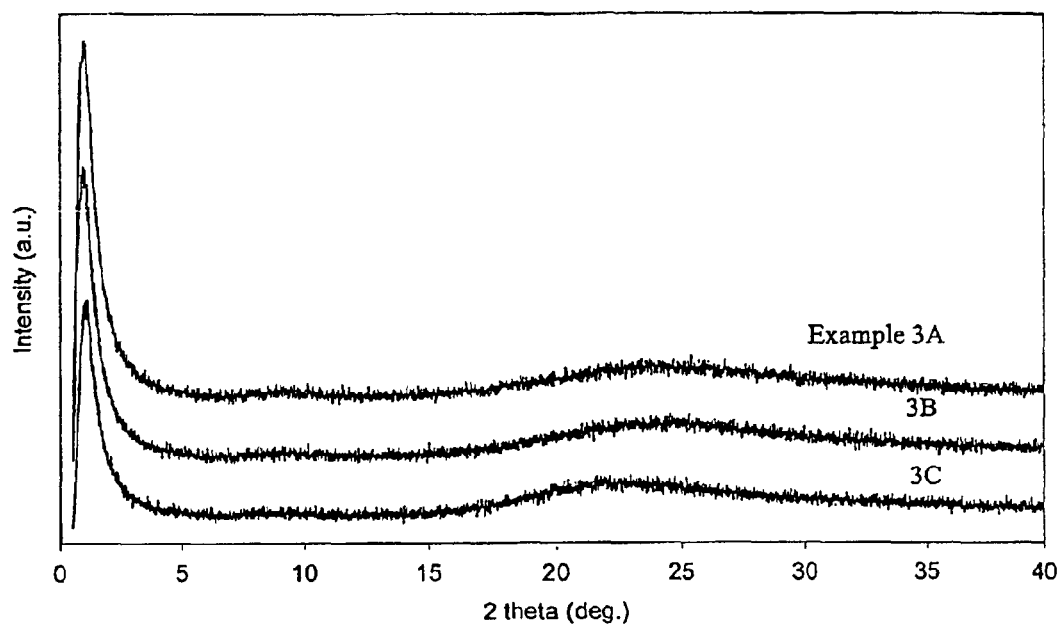
FIG. 5 shows the XRD patterns of the mesoporous materials of Examples 3A, 3B and 3C.
Figure 6:
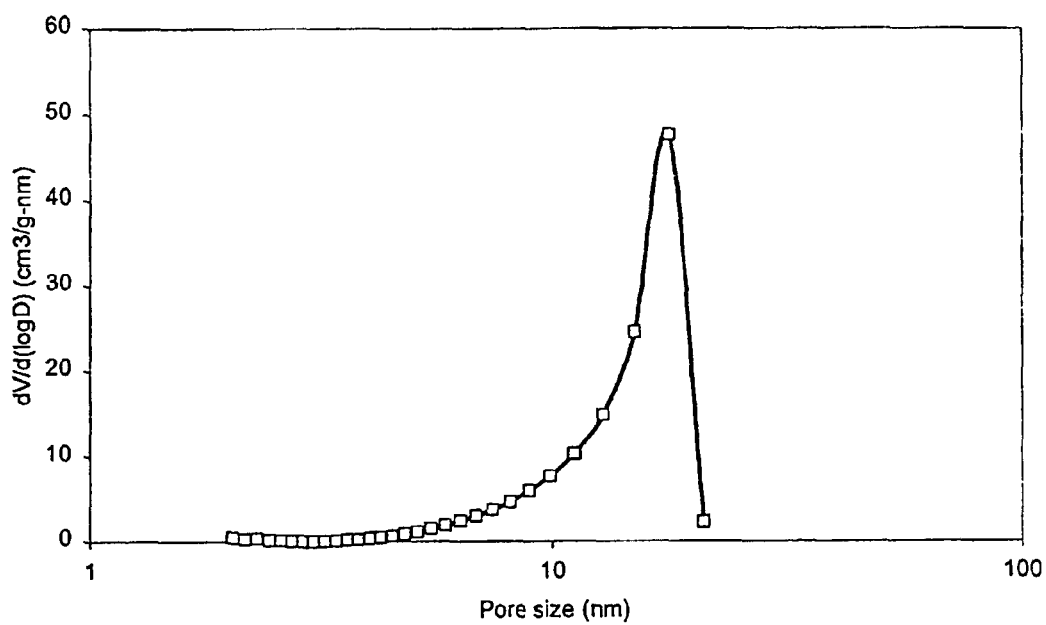
FIG. 6 is a graph illustrating the pore size distribution of the mesoporous material of Example 3A.

Elemental analysis showed the Si/Al ratio to be 99.2. FIG. 5 shows its XRD pattern with an intensive peak. Nitrogen adsorption shows a narrow pore size distribution centered at 17 nm, as presented in FIG. 6, which exhibited a surface area of about 385 m²/g, and a pore volume of about 1.32 cm³/g.

EXAMPLE 3B

The material obtained in Example 3A was boiled in water for 17 hours, but its XRD pattern, seen in FIG. 5, still shows an intensive peak, similar to the original material. It indicates that this composition has high hydrothermal stability compared to other mesoporous materials.

EXAMPLE 3C

The material obtained in Example 3A was calcined at 900° C. in air, but its XRD pattern (FIG. 5) still shows an intensive peak, indicating that the mesoporous structure was preserved. This result indicates that this composition has high thermal stability up to 900° C.

EXAMPLE 4

This is an example to use inorganic heteroatom sources to incorporate aluminum into silica. 7.2 Parts of aluminum nitrate nonahydrate were dissolved into 20 parts of water. Then, 61.4 parts of TEOS were added and stirred for 0.5 hours. Another mixture with 56.3 parts of tetraethylene glycol and 24 parts of water were added into the above mixture under stirring. After 1 hour stirring, 49 parts of aqueous solution of tetraethylammonium hydroxide (TEAOH, 35 wt %) were added and after 0.5 hours stirring the final mixture turned into a thick gel. The gel was dried in an oven at 100° C. overnight and then transferred into an autoclave at 180° C. for 3 hours. Finally, it was calcined at 600° C. for 10 hours with a ramp rate of 1° C./min in air.

Elemental analysis showed the Si/Al ratio of 15.3. Its XRD pattern showed an intensive peak at about 1 degree in 2 θ. Nitrogen adsorption revealed a narrow pore size distribution centered at 4.5 nm, a specific surface area of about 786 m²/g, and a total pore volume of about 1.02 cm³/g.

EXAMPLE 5

This illustrates the incorporation of vanadium into silica. 1 Part of vanadium (IV) acetylacetonate was added into a bottle with 41 parts of TEOS and stirred for 2 hours. A mixture of 30 parts of TEA and 25 parts of water were added into the above mixture under stirring. After 2 hours stirring, 20 parts of TEAOH was drop-wise added into the above mixture and after 0.5 hours stirring it turned into a hard gel. The gel was aged at room temperature for 24 hours and dried in an oven at 100° C. overnight and then calcined at 700° C. for 10 hours in air and finally turned into orange powder.

Figure 7:
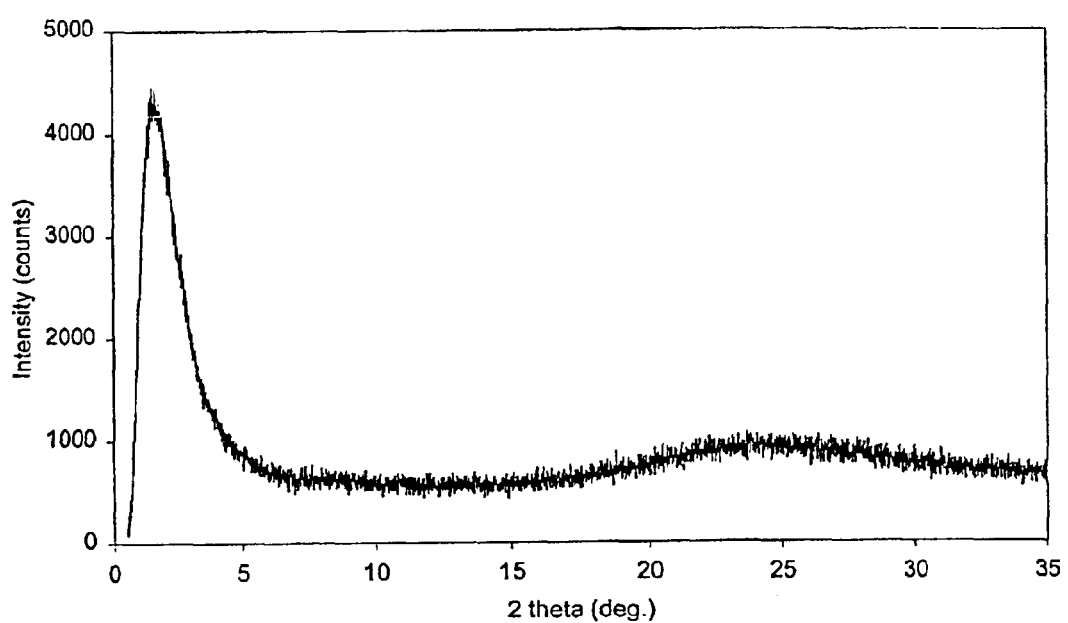
FIG. 7 is an XRD pattern of the vanadium-containing mesoporous material of Example 5.

Elemental analysis showed the Si/V ratio to be 50.5. FIG. 7 shows its XRD pattern with an intensive peak for mesostructure and without any peaks from vanadium oxide phases. Nitrogen adsorption showed a narrow pore size distribution centered at 4.1 nm, a specific surface area of about 835 m²/g, and a pore volume of about 0.91 cm³/g.

EXAMPLE 6

Here, titanium incorporation is demonstrated. 1 Part of titanium(IV) butoxide was added into a bottle with 31 parts of TEOS and stirred for 2 hours. A mixture of 22.5 parts of TEA and 17 parts of water were added into the above mixture under stirring. After 1 hour stirring, 18.5 parts of TEAOH were drop-wise added into the above mixture and after 0.5 hours stirring it turned into a thick gel. The gel was aged at room temperature for 22 hours and dried in an oven at 98° C. overnight and then calcined at 700° C. for 10 hours in air and finally turned into white powder.

Figure 8:
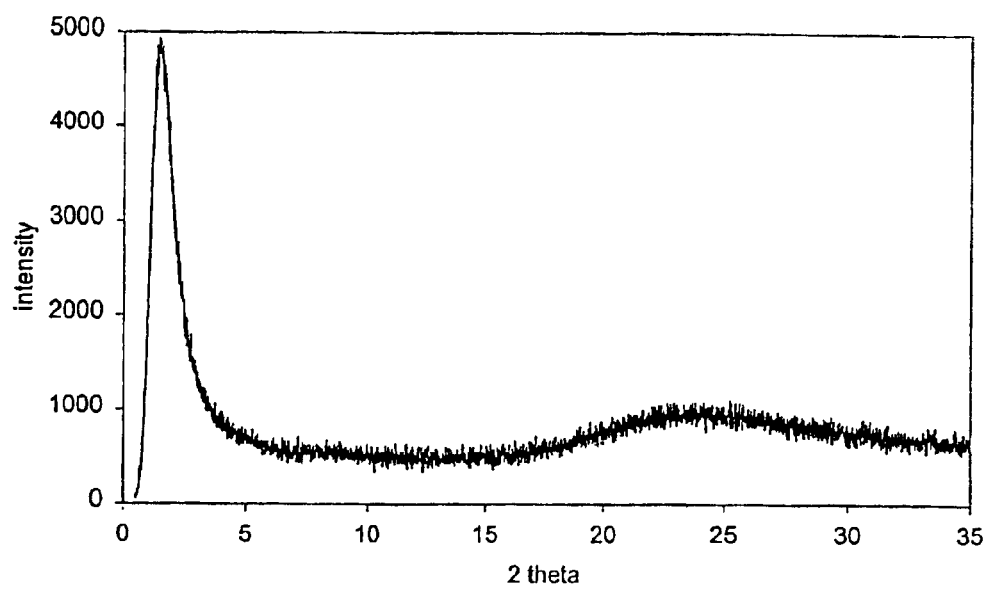
FIG. 8 is an XRD pattern of the titanium-containing mesoporous material of Example 6.
Figure 9:
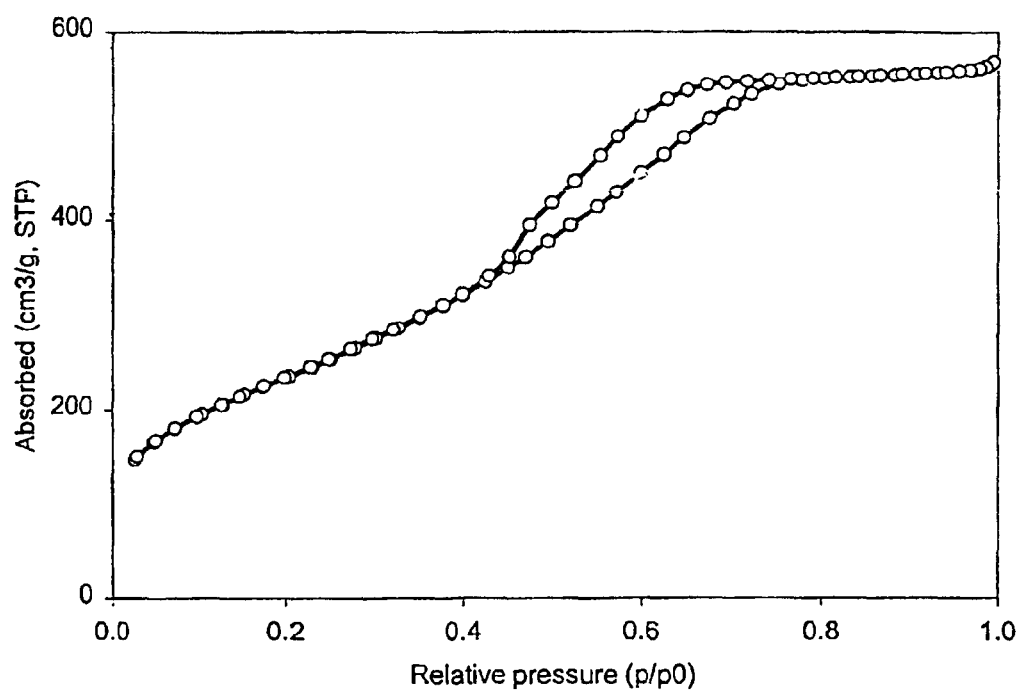
FIG. 9 is a graph illustrating the nitrogen sorption isotherms of the titanium-containing mesoporous material of Example 6.
Figure 10:
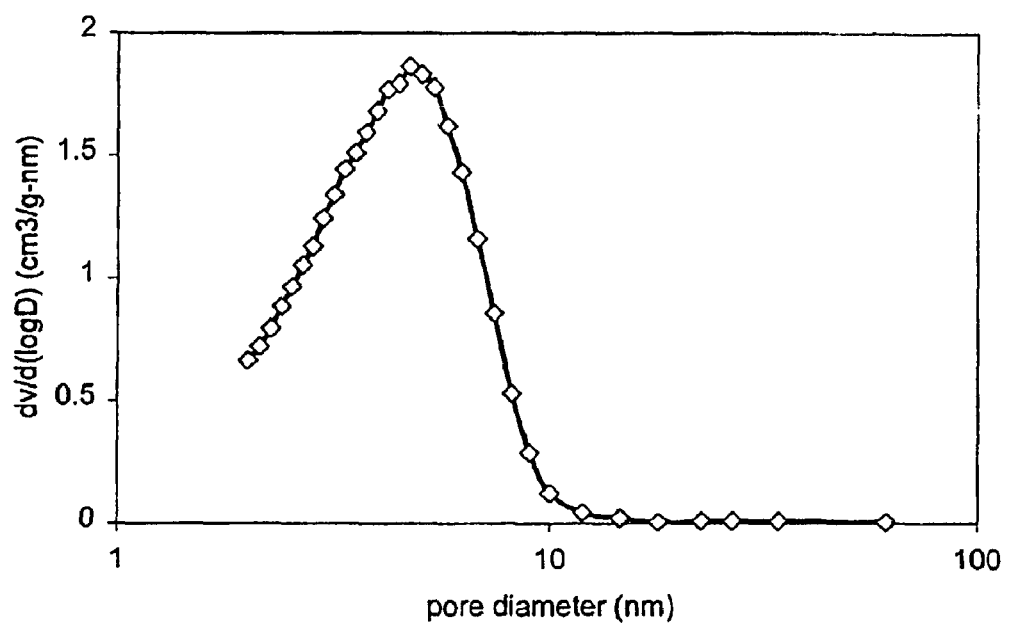
FIG. 10 is a graph illustrating the pore size distribution of the titanium-containing mesoporous material of Example 6.

Elemental analysis showed the Si/Ti ratio to be 49.6. FIG. 8 shows its XRD pattern with an intensive peak for mesostructure and no resolved peak for titanium oxide. Nitrogen sorption isotherms are shown in FIG. 9, which revealed pore size distribution centered at 4.7 nm, shown in FIG. 10, a specific surface area of about 917 m²/g, and a total pore volume of about 0.84 cm³/g.

EXAMPLES 7–9

Here is a demonstration of the incorporation of three different heteroatoms. 42 Parts of tetraethyl orthosilicate (TEOS) were mixed with 30 parts of triethanolamine (TEA) for 1 hour to get mixture I. Mixture II was prepared by dissolving heteroatom sources into 22 parts of water. 1 Part of gallium nitrate, 0.54 parts of zinc chloride and 0.9 parts of tin chloride were used for Examples 7, 8 and 9, respectively. Mixture II was drop-wise added into the mixture I under stirring. After the combined mixtures I and II were stirred for 0.5 hours, 24.5 parts of tetraethylammonium hydroxide were drop-wise added while stirring. After being stirred for 2 hours, the three mixtures were each observed to be clear solutions and finally 0.5 g of ammonium hydroxide (27–30 wt %) was added. After being stirred for another 2 hours, the mixtures were statically aged overnight. The mixtures were dried at 98° C. for 24 hours and each turned into dried gel. The dried gels were charged into autoclave at 180° C. for 2.5 hours and finally were calcined at 600° C. in air for 10 hours.

Figure 11:
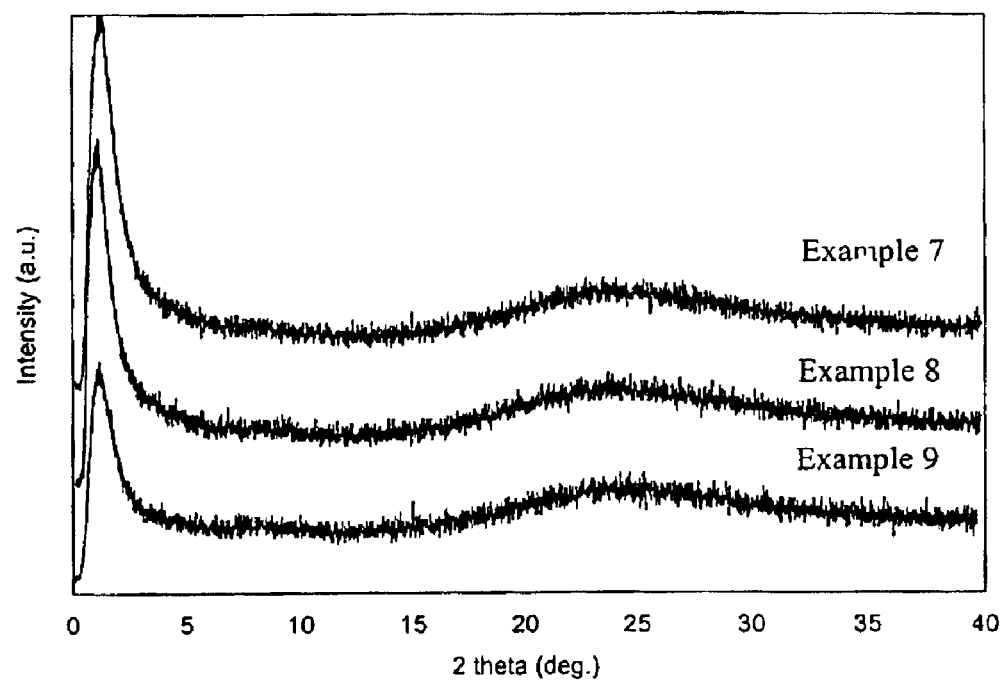
FIG. 11 shows the XRD patterns of the mesoporous materials of Examples 7, 8, and 9.

FIG. 11 shows XRD patterns of gallium, zinc and tin-containing silicates prepared in Examples 7, 8 and 9, respectively. Table 1 presents the mesoporosity and chemical composition of three materials.

TABLE 1

Mesoporosity of gallium-, zinc- and tin-containing silicates in Examples 7, 8 and 9, respectively

| Example | Heteroatom M | M content (wt %) | $D_p$* (nm) | $S_{BET}$* (m²/g) | $V_{total}$* (cm³/g) |
|---|---|---|---|---|---|
| 7 | Ga | 1.3 | 4 | 830 | 0.71 |
| 8 | Zn | 1.9 | 5 | 690 | 0.69 |
| 9 | Sn | 3.3 | 4.5 | 780 | 0.67 |

*$D_p$ stands for pore diameter, $S_{BEP}$ for specific surface area, $V_{total}$ for total pore volume.

EXAMPLE 10

This example demonstrates the simultaneous incorporation of two types of heteroatoms into silica. First, 2.7 parts of aluminum isopropoxide were mixed with 0.86 parts of vanadium (IV) acetylacetonate and 34 parts of tetraethyl orthosilicate (TEOS) to get the first mixture. The second mixture contained 34 parts of TEA and 21 parts of water. Then the second mixture was drop-wise added into the first mixture under stirring. After stirred for 1.5 hours, 16.8 parts of tetraethylammonium hydroxide were drop-wise added while stirring. The synthesis mixture turned into a thick gel. The gel was statically aged at room temperature overnight, dried at 100° C. for 42 hours and then heated in an autoclave at 180° C. for 3 days. Finally, it was calcined at 650° C. in air for 10 hours.

Figure 12:
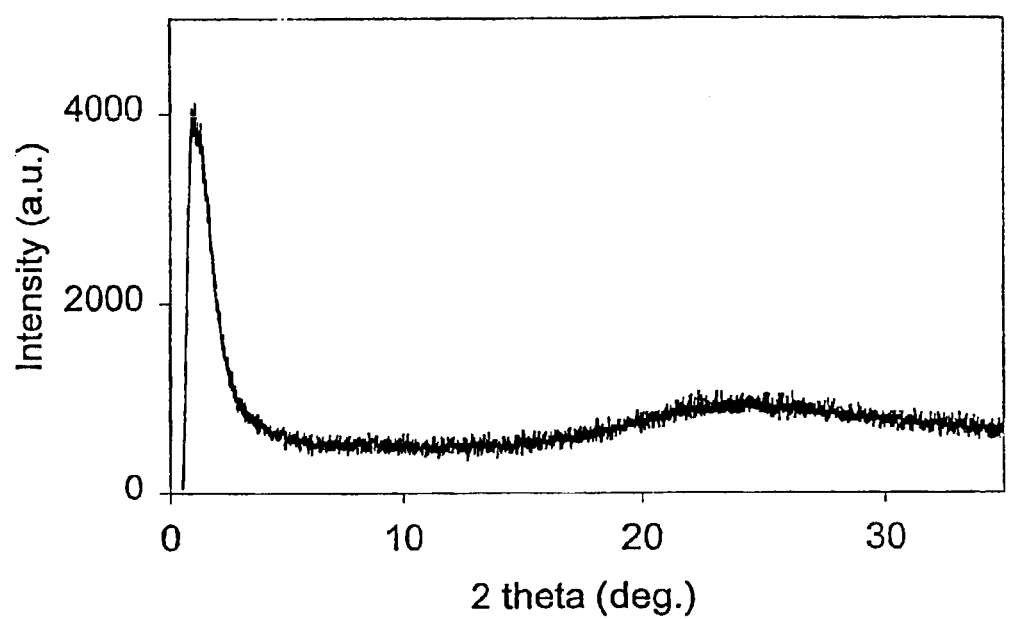
FIG. 12 is an XRD pattern of the aluminum and vanadium-containing mesoporous material of Example 10.
Figure 13:
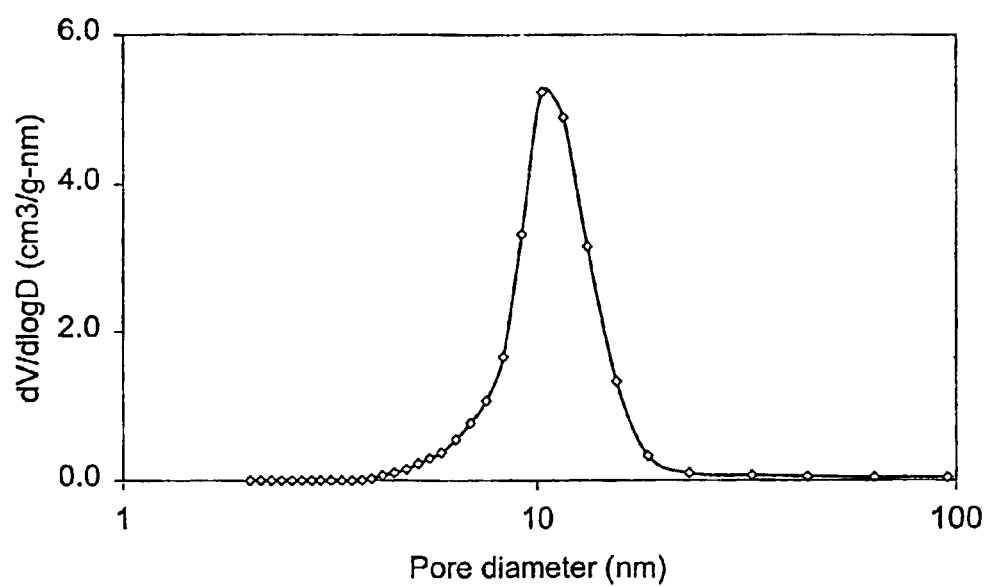
FIG. 13 is a graph illustrating the pore size distribution of the aluminum and vanadium-containing mesoporous material of Example 10.

FIG. 12 shows the XRD pattern of the aluminum and vanadium-containing silicate. Nitrogen adsorption revealed that it had a narrow pore size distribution around 11 nm (shown in FIG. 13), a surface area of about 433 $m^2/g$ and total pore volume of about 1.25 $cm^3/g$. Elemental analysis showed that Si/Al=13.5 and Si/V=49.1.

EXAMPLE 11

This example demonstrates the preparation of Fe-containing mesoporous silicate. One part of iron (III) nitrate was dissolved in 5 parts of deionized water and then added to 27.4 parts of tetraethyl orthosilicate (TEOS) and stirred for 1 hour. Another solution consisting of 19.8 parts of triethanolamine (TEA) and 30.4 parts of deionized water were introduced drop-wise into the first mixture. After another 1 h of stirring, 16.2 parts of tetraethylammonium hydroxide (TEAOH) were drop-wise added to the mixture. The final homogeneous pale yellow solution was aged at room temperature for 24 hours, dried at 100° C. for 24 hours, and finally calcined at 650° C. for 10 hours to get a pale yellow powder.

Figure 14:
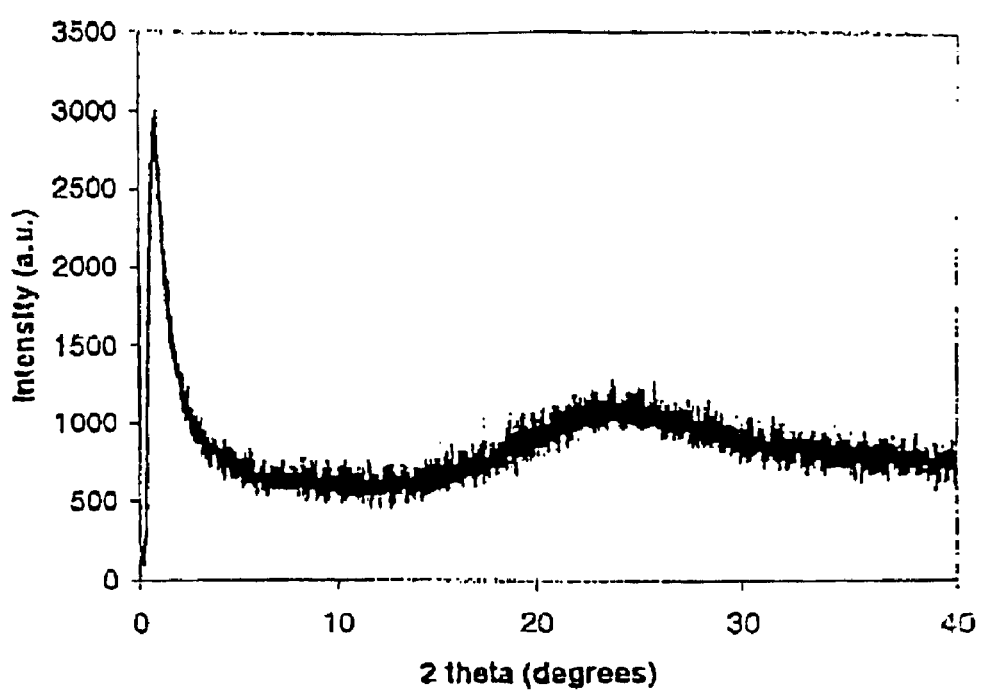
FIG. 14 is an XRD pattern of the iron-containing mesoporous material of Example 11.
Figure 15:
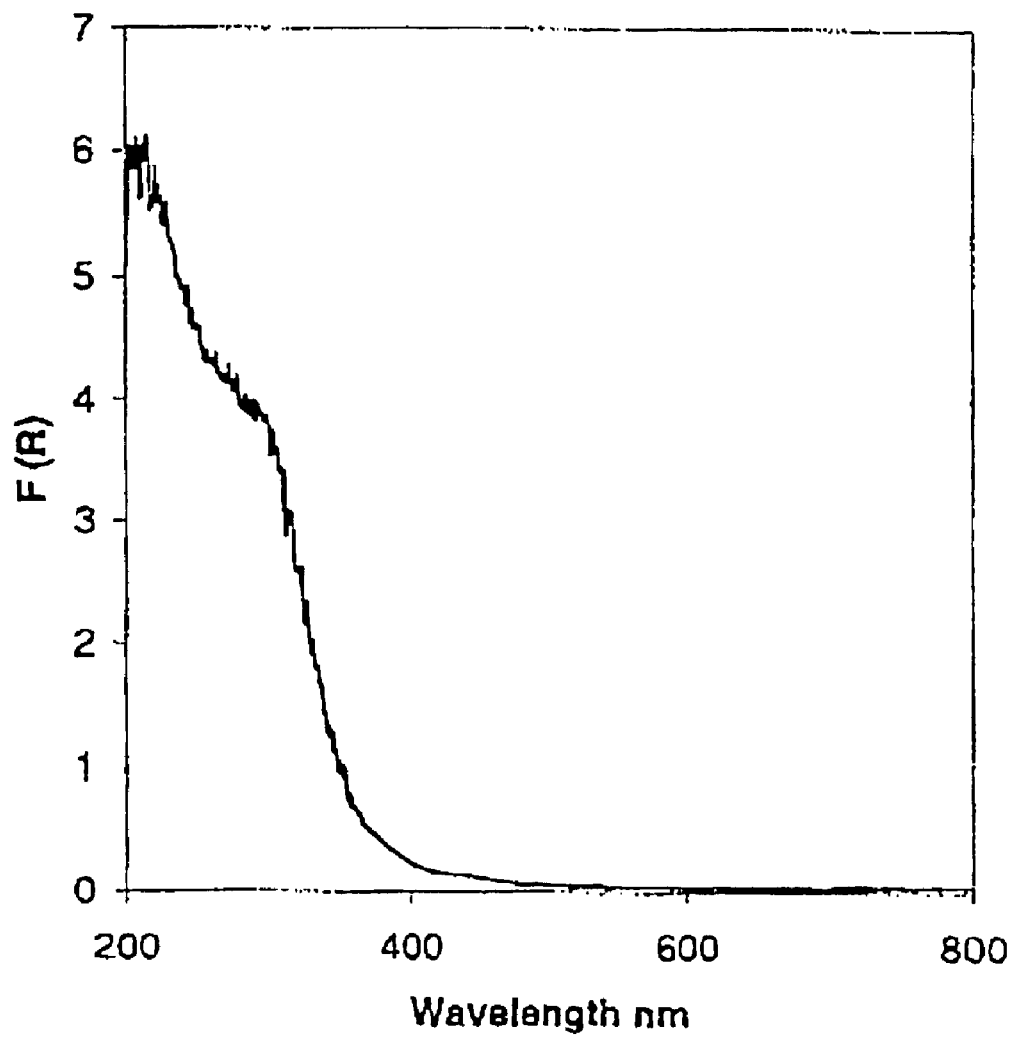
FIG. 15 shows the UV-Visible spectrum of the iron-containing mesoporous material of Example 11.
Figure 16:
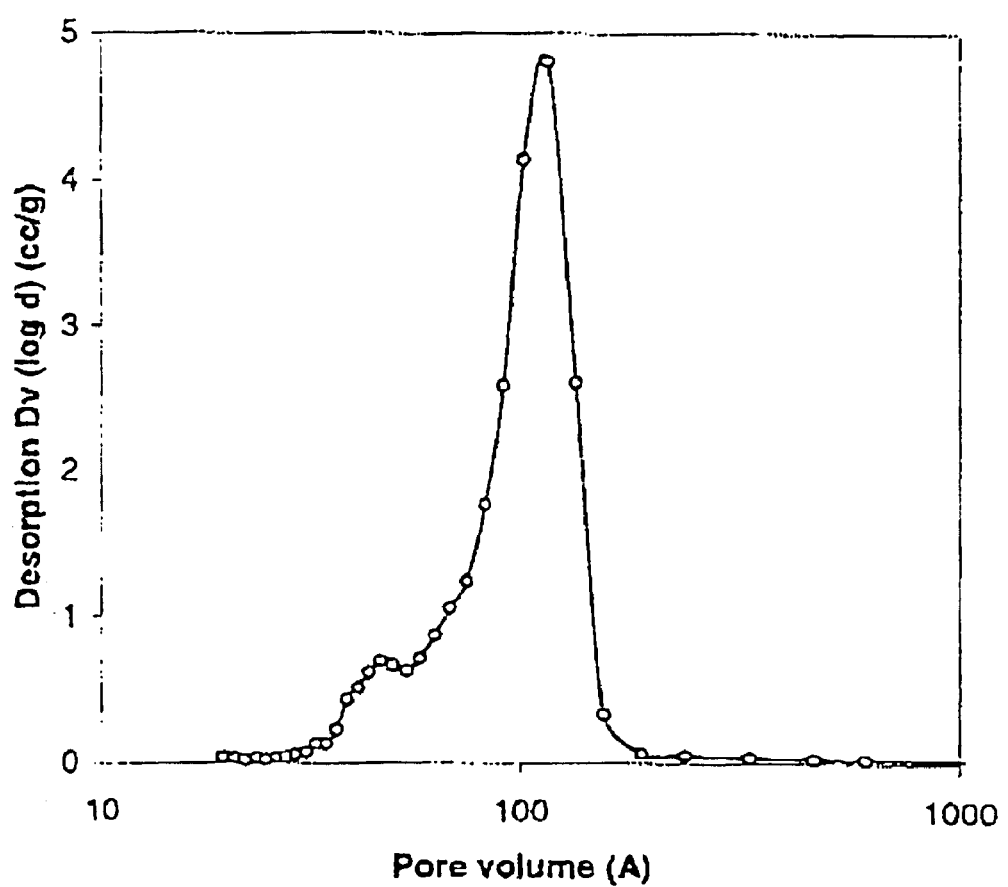
FIG. 16 is a graph showing the pore size distribution of the iron-containing mesoporous material of Example 11.

FIG. 14 shows the XRD pattern with one intensive peak at a low angle of about 0.5~2.2°, representing the mesostructural characteristics. Elemental analysis showed the atomic ratio of Si/Fe was 48.8. UV-Visible spectroscopy (FIG. 15) showed a peak around 220 nm, representing the four coordinated iron, and also a shoulder ranged from 250~350 nm, representing the octahedral coordination of iron in the silica matrix. $N_2$ adsorption measurements revealed the BET surface area of about 630 $m^2/g$, the average mesopore diameter of about 4.8 nm (cf. FIG. 16), and the total pore volume of about 1.24 $cm^3/g$.

EXAMPLE 12

The procedure of making Fe-containing silicate is similar to that in Example 11; however, only 0.52 part of iron (III) nitrate was used. After calcination, the elemental analysis showed that the powder has a Si/Fe atomic ratio of 98.6. Nitrogen adsorption showed a specific surface area of 580 $m^2/g$, an average pore diameter of 5.96 nm, and a pore volume 1.82 $cm^3/g$.

EXAMPLE 13

This demonstrates the preparation of Cr-containing silicate. 1.2 Parts of chromium nitrate nonahydrate were dissolved in 5 parts of deionized water and then added to 26.3 parts of tetraethyl orthosilicate (TEOS) and stirred for 1 hour. Another solution consists of 19 parts of triethanolamine (TEA) and 22.2 parts of deionized water were introduced drop-wise into the above solution. After another 1 hour of stirring, 26.2 parts of tetraethylammonium hydroxide (TEAOH) were added drop-wise to the mixture. The final homogeneous pale green solution was aged at room temperature for 24 hours, dried at 100° C. for 24 hours, and finally calcined at 650° C. for 10 hours to get a yellowish orange powder containing chromium.

Figure 17:
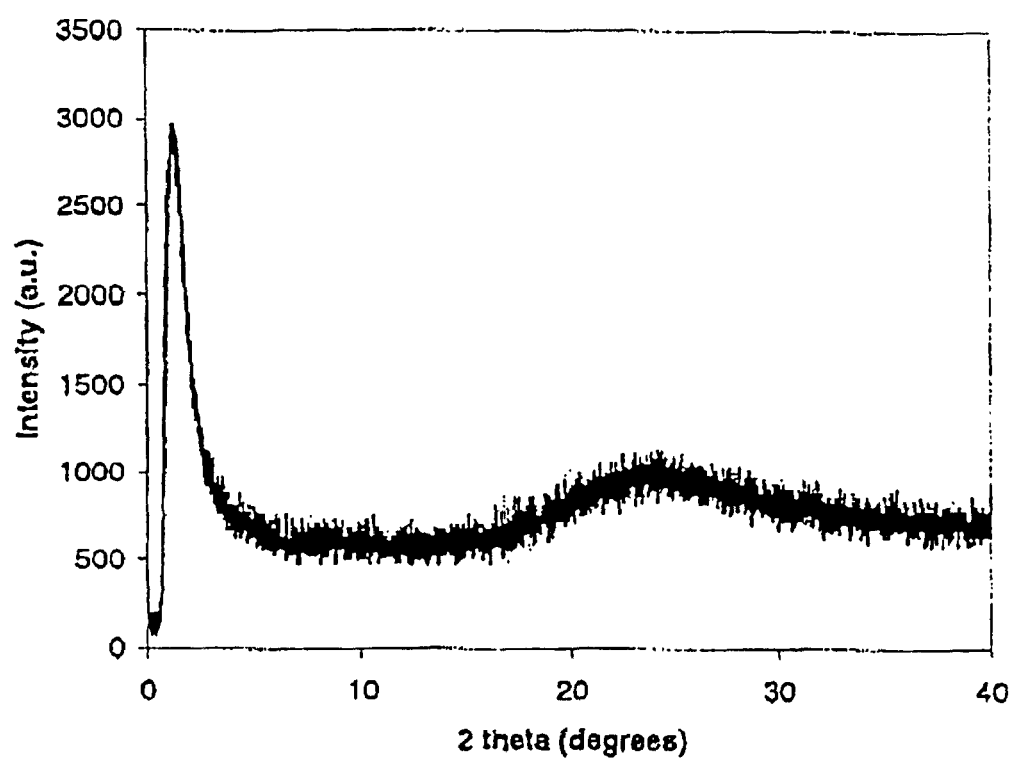
FIG. 17 is an XRD pattern of the chromium-containing mesoporous material of Example 13.
Figure 18:
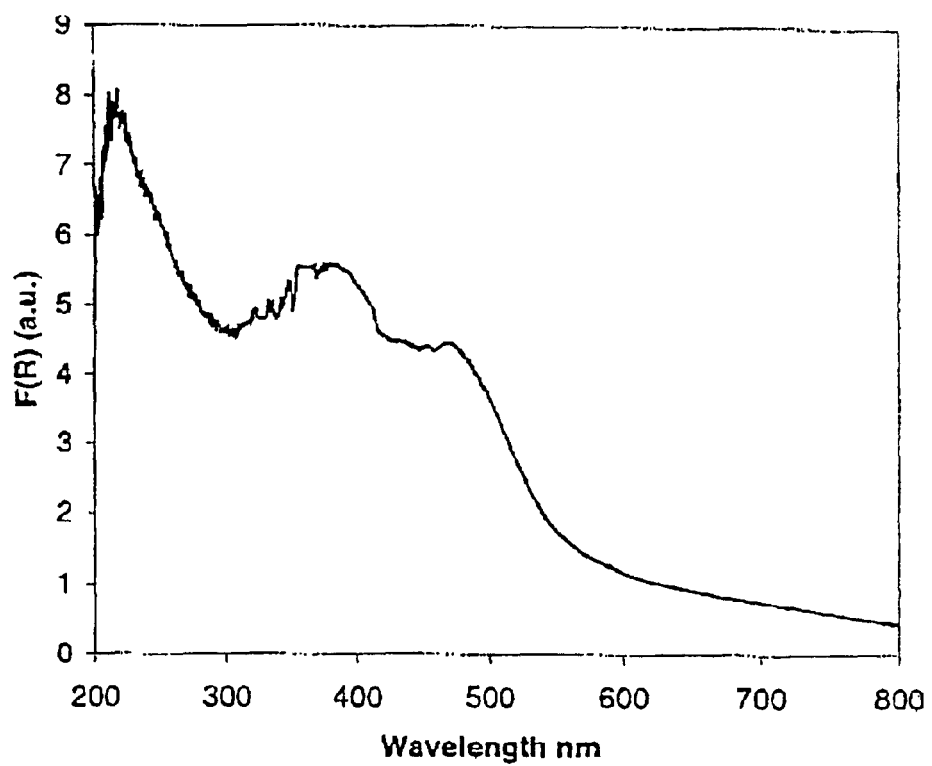
FIG. 18 shows the UV-Visible spectrum of the chromium-containing mesoporous material of Example 13.
Figure 19:
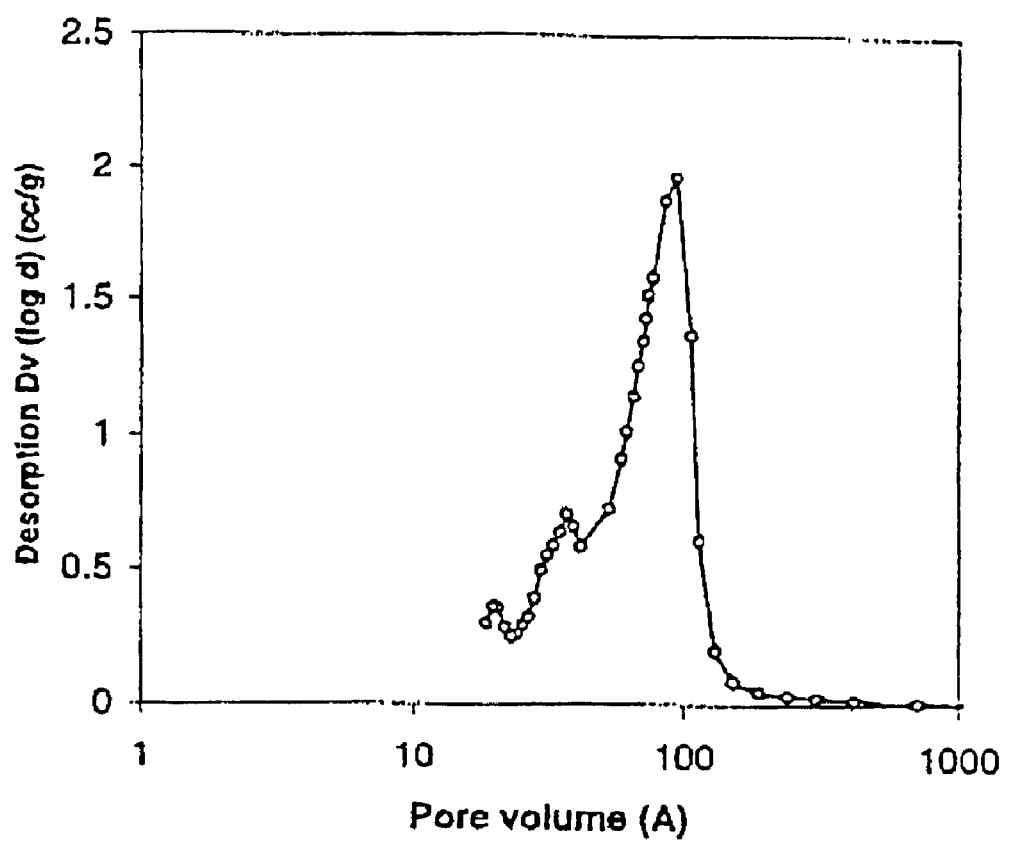
FIG. 19 is a graph showing the mesopore size distribution of the mesoporous material of Example 13.

FIG. 17 shows the XRD pattern with one intensive peak at a low angle of about 0.5~2.2° representing the mesostructural characteristics. UV-Visible spectroscopy (FIG. 18) showed two distinguishing peaks around 220 and 390 nm, representing the four coordinated chromium, and also a shoulder around 480 nm representing the octahedral coordination of polychromate (—Cr—O—Cr—)$_n$ in the silica matrix. $N_2$ adsorption measurements revealed the BET surface area of about 565 $m^2/g$, the average mesopore diameter of 1.96 nm (cf. FIG. 19), and the total pore volume of about 1.54 $cm^3/g$.

EXAMPLE 14

The procedure of making Cr-mesoporous silicate is similar to that in Example 13; however, 1.31 parts of chromium nitrate were used. After calcination, the elemental analysis showed that the powder has a Si/Cr atomic ratio of 40:3. Nitrogen adsorption showed specific surface area of 572 $m^2/g$, pore diameter of 2.35 nm and pore volume of 1.7 $cm^3/g$.

EXAMPLE 15

The preparation of the composition containing Mo is demonstrated here. 1.6 parts of ammonium heptamolybdate tetrahydrate solution [$(NH_4)_6Mo_7O_{24}.4H_2O$] were dissolved in 5 parts of deionized water and then added to 27.1 parts of tetraethyl orthosilicate (TEOS) and stirred for 1 hour. Another solution consists of 19.6 parts of triethanolamine (TEA) and 30.4 parts of deionized water were introduced drop-wise into the above solution. After another 1 hour of stirring, 16.1 parts of tetraethylammonium hydroxide (TEAOH) were added drop-wise to the mixture. The final homogeneous pale yellow solution was aged at room temperature for 24 hours, dried at 100° C. for 24 hours, and finally calcined at 650° C. for 10 hours to get a white powder.

Figure 20:
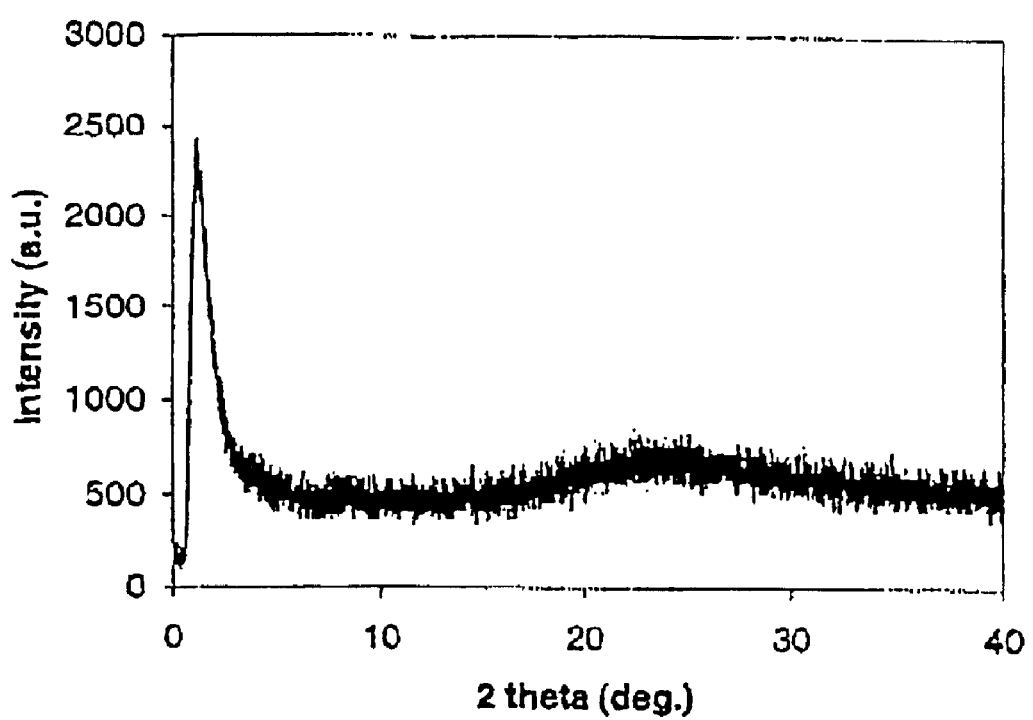
FIG. 20 is an XRD pattern of the molybdenum-containing mesoporous material of Example 15.
Figure 21:
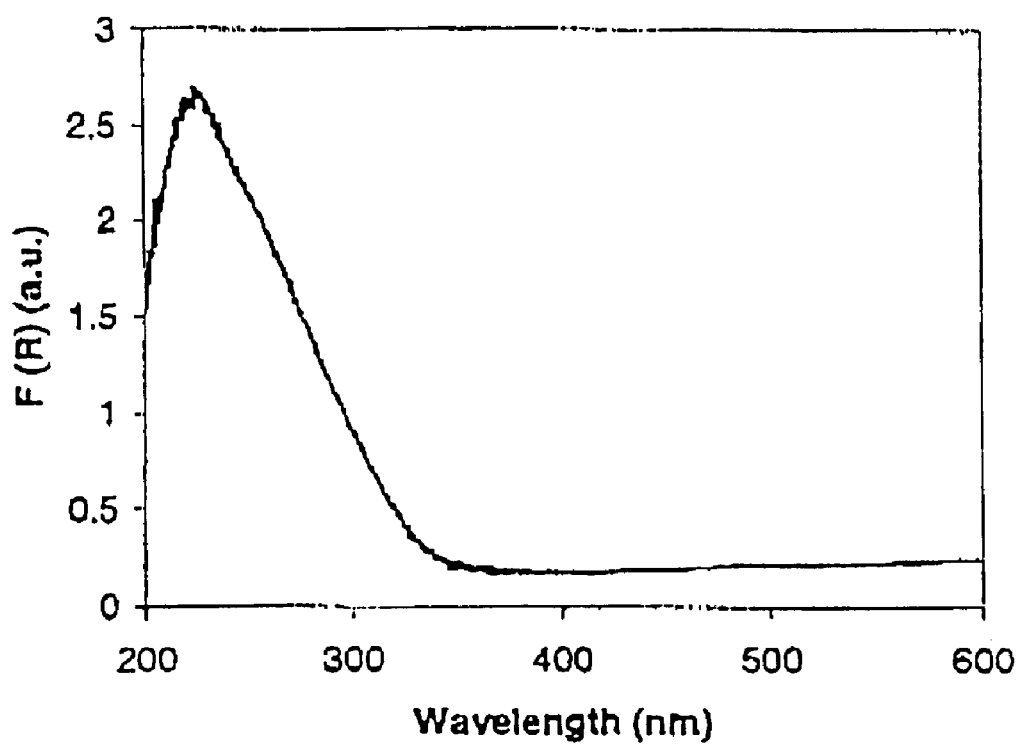
FIG. 21 shows the UV-Visible spectrum of the mesoporous material of Example 15; and, FIG. 22 is a graph showing the mesopore size distribution of the mesoporous material of Example 15.
Figure 22:
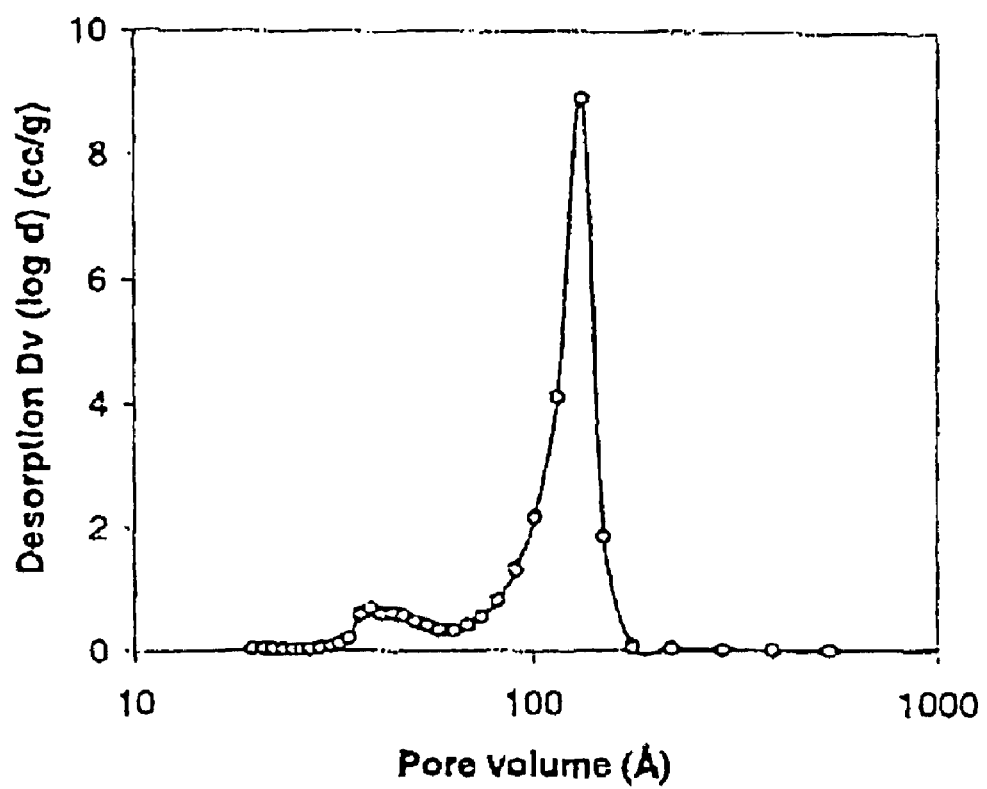

FIG. 20 shows the XRD pattern with one intensive peak at a low angle of about 0.5~2.2°, representing the mesostructural characteristics. UV-Visible spectroscopy (FIG. 21) shows a peak around 220 nm representing four-coordinated molybdenum in the silica matrix. $N_2$ adsorption measurements revealed the BET surface area of about 500 $m^2/g$, the average mesopore diameter of about 8.91 nm (cf. FIG. 22), and the total pore volume of about 1.31 $cm^3/g$.

EXAMPLE 16

The procedure of making Mo-mesoporous silicate is similar to that in Example 15; however, 3.9 parts of ammonium heptamolybdate tetrahydrate solution [$(NH_4)_6Mo_7O_{24}.4H_2O$] were used. After calcining, the elemental analysis showed that the powder has a Si/Mo atomic ratio of 39.8. Nitrogen adsorption indicated a specific surface area of 565 $m^2/g$, an average pore diameter of 3.93 nm, and pore volume of 0.98 $cm^3/g$.

EXAMPLE 17

Simultaneous incorporation of both Ni and Mo into a mesoporous material is demonstrated. First, 7.7 parts of nickel (II) nitrate hexahydrate and 32 parts of ammonium heptamolybdate tetrahydrate were dissolved into 54 parts of water under stirring. Then, 67 parts of tetraethyl orthosilicate (TEOS) were added into the above solution under vigorous stirring. After stirring for 1.5 hours, 40 parts of tetraethylammonium hydroxide (TEAOH) were drop-wise added while stirring. The synthesis mixture turned into a thick gel. The gel was statically aged at room temperature overnight, dried at 100° C. for 24 hours and then heated in an autoclave at 180° C. for 3 hours. Finally, the synthesis mixture was calcined at 600° C. in air for 10 hours.

The XRD pattern of the final powder shows an intensity peak at around 1.1 degree 2 θ, indicating the characteristics of mesoporous material. Nitrogen adsorption reveals that it has a narrow pore size distribution around 2.3 nm, a surface area of about 633 $m^2/g$ and total pore volume of about 0.86 $cm^3/g$. Elemental analysis shows the final powder contained 6.1 wt % of Ni and 10.5 wt % of Mo.

EXAMPLE 18

This example demonstrates simultaneous incorporation of both Ni and W into a mesoporous material. First, 5.8 parts of nickel (II) nitrate hexahydrate and 35 parts of ammonium metatungstate hydrate were dissolved into 42.3 parts of water under stirring. Then 50.5 parts of tetraethyl orthosilicate (TEOS) were added into the above solution under vigorous stirring. After stirring for 1.5 hours, 30.0 parts of tetraethylammonium hydroxide were drop-wise added while stirring. The synthesis mixture turned into a thick gel. The gel was statically aged at room temperature overnight, dried at 100° C. for 24 hours and then heated in an autoclave at 180° C. for 3 hours. Finally, it was calcined at 600° C. in air for 10 hours.

The XRD pattern of the final powder shows an intensity peak at around 1.0 degree 2 θ, indicating the characteristics of mesoporous material. Nitrogen adsorption reveals that it has a narrow pore size distribution around 2.4 nm, a surface area of about 649 $m^2/g$ and total pore volume of about 0.81 $cm^3/g$. Elemental analysis shows the final powder contained 6.4 wt % of Ni and 12.0 wt % of W.

EXAMPLE 19

The preparation of a palladium-containing catalyst was demonstrated. 65 Parts of the material in Example 1 was mixed with 35 parts alumina and water is added to this mixture to allow the resulting catalyst to be extruded. The catalyst was calcined at 480° C. in 5 v/v/min nitrogen for 6 hours followed by the replacement of the nitrogen flow with 5 v/v/min of air. The calcining was completed by raising the temperature to 540° C., maintaining that temperature for 12 hours. Palladium was incorporated by impregnation with an aqueous solution of a palladium tetraamine salt, $Pd(NH_3)_4Cl_2$. The extrudate was then dried at 120° C. overnight and calcined at 300° C. in air for 3 hours. The final catalyst has 0.81 wt. % of palladium, surface area of 630 $m^2/g$, particle density of 0.83 g/ml, and pore volume of 1.21 $cm^3/g$.

EXAMPLE 20

Alkylation of naphthalene with 1-hexadecene was carried out in a flask with mechanical stirring. Catalysts of Examples 1, 2, and 3A were used. 1 Part of catalyst was loaded in the flask and heated up to 200° C. under vacuum for 2 hours. After the catalyst was cooled down to 90–100° C. under nitrogen, a mixture consisting of 6.5 weight parts of naphthalene and 26 parts of 1-hexadecene was injected into the flask under stirring. The temperature was raised up to 200–205° C. and kept constant. The reaction mixture was analyzed by gas chromatography with WAX 52 CB column. Reaction results using different catalysts are summarized in Table 2.

TABLE 2

Naphthalene alkylation with 1-hexadecene over different catalysts

| Catalyst | Composition | Reaction time (hr) | Naphthalene conversion (%) | Selectivity* (%) |
|---|---|---|---|---|
| Example 1 | Si/Al = 24.8 | 4 | 25.6 | 57.6 |
| Example 2 | Si/Al = 24.5 | 4.5 | 27.3 | 56.7 |
| Example 3A | Si/Al = 99.2 | 4 | 19.6 | 65.3 |

*The selectivity refers to the selectivity towards monoalkylated naphthalene.

EXAMPLE 21

Friedel-Crafts alkylation of benzene with chlorobenzene was conducted in a flask with magnetic stirring. Catalysts of Examples 7, 9, 11 and 12 were used. 1 Part of the catalyst was loaded in the flask and heated up to 180° C. under vacuum for 4 hours. After the catalyst was cooled down to 80° C. under nitrogen, a mixture consisting of 102 parts of benzene and 8.2 parts of benzyl chloride were introduced into the flask. The temperature was constantly kept at 60° C. or 80° C. The reaction mixture was analyzed by gas chromatography with WAX 52 CB column. Reaction results using different catalysts are summarized in Table 3.

TABLE 3

Benzylation of benzene to produce diphenyl methane over different catalysts

| Catalyst | Composition | Reaction time (min.) | Temperature (° C.) | Conversion (%) | Selectivity (%) |
|---|---|---|---|---|---|
| Example 12 | Si/Fe = 98.6 | 240 | 60 | 86 | 100 |
| Example 11 | Si/Fe = 50.1 | 60 | 60 | 51 | 100 |
| Example 11 | Si/Fe = 50.1 | 150 | 60 | 100 | 100 |
| Example 11 | Si/Fe = 50.1 | 60 | 80 | 97 | 100 |
| Example 7 | Si/Ga = 71 | 240 | 60 | 64.9 | 100 |
| Example 9 | Si/Sn = 46 | 240 | 60 | 15.8 | 100 |

EXAMPLE 22

Selective oxidation of ethylbenzene to acetophenone was performed in a flask under nitrogen with stirring. Catalysts of Examples 13, 14 and 16 were used. One part of the catalyst was activated at 180° C. for 4 hours under vacuum, and then the cooled down to 80° C. Then a mixture consisting of 100 parts of acetone, 82 parts of ethylbenzene and 9.5 parts of tert-butyl hydroperoxide (TBHP) were introduced to the flask under stirring. The reaction mixture was analyzed by gas chromatography with WAX 52 CB column. Reaction results over various catalysts are summarized in Table 4.

TABLE 4

Conversion of ethylbenzene to acetophenone over different catalysts.

| Catalyst | Composition | Time | Gas flow | Temperature | Conversion | Selectivity |
|---|---|---|---|---|---|---|
| Example 13 | Si/Cr = 130 | 480 | Dry $N_2$ | 80 | 68.5 | 94.5 |
| Example 13 | Si/Cr = 130 | 480 | air | 80 | 73.6 | 95.3 |
| Example 13 | Si/Cr = 130 | 480 | air | 60 | 54.7 | 99.3 |

TABLE 4-continued

Conversion of ethylbenzene to acetophenone over different catalysts.

| Catalyst | Composition | Time | Gas flow | Temperature | Conversion | Selectivity |
|---|---|---|---|---|---|---|
| Example 14 | Si/Cr = 40.3 | 480 | air | 80 | 67.3 | 92.9 |
| Example 16 | Si/Mo = 39.8 | 360 | air | 80 | 24.2 | 58.9 |

EXAMPLE 23

Oligomerization of 1-decene was performed in a stirred batch reactor. The catalyst of Example 2 was used. In the reactor 1 part of catalyst was activated by heating in nitrogen at 200° C. for 2 hours. 25 Parts of 1-decene were added by syringe under nitrogen flow. The reaction was carried out at 150° C. for 24 hours. After the reactor was cooled down, the product was analyzed by gas chromatography (GC) with a WAX 52 CB column. For each test, mole % decene conversion and dimer selectivity is presented in Table 5.

TABLE 5

Oligomerization of 1-decene over different catalysts

| Catalyst | Composition | Time | Temperature | Conversion |
|---|---|---|---|---|
| Example 2 | Si/Al = 24.5 | 4 | 150 | 12.6 |
| Example 2 | Si/Al = 24.5 | 24 | 150 | 25.8 |

EXAMPLE 24

Acylation of 2-methoxynaphthalene to 2-acetyl-6-methoxynaphthalene is performed in a stirred batch reactor. The reactor with 16 parts of catalysts made in Example 2 is heated at 240° C. under vacuum for 2 hours and then filled with dry nitrogen. After the reactor is cooled down to 120° C., 250 parts of decalin (as a solvent), 31 parts of 2-methoxynaphthalene, 42 parts of acetic anhydride and 10 parts of n-tetradecane (as an internal standard) are injected into the reactor. After 6 hours reaction, the reactor mixture is analyzed by GC with a WAX 52 CB column, and it is found that the conversion of 2-methoxynaphthalene reaches 36.5% with 100% selectivity to 2-acetyl-6-methoxynaphthalene.

EXAMPLE 25

Oxidation of cyclohexanol to cyclohexanone was carried out in a stirred batch reactor. The reactor with 1 part of catalysts is heated at 180° C. under vacuum for 4 hours and then filled with dry nitrogen. After cooled down to 55° C., 100 parts of acetone, 10 part of tert-butyl hydroperoxide (TBHP) and 7.5 parts of cyclohexanol were introduced the flask; and the reaction temperature was kept at 55° C. After 5 hours reaction, the reactor mixture is analyzed by GC with WAX 52 CB column; and the performance of different catalysts was summarized in Table 6.

TABLE 6

Oxidation of cyclohexanol to cyclohexanone over various catalysts

| Catalyst | Composition | Temperature (° C.) | Time (hr) | Conversion (%) | Selectivity (%) |
|---|---|---|---|---|---|
| Example 15 | Si/Mo = 97.9 | 55 | 5 | 79.4 | 95 |
| Example 16 | Si/Mo = 39.8 | 55 | 5 | 84.6 | 93 |

EXAMPLE 26

The material of Example 17 was evaluated for upgrading Paraho shale oil at 68 bar $H_2$ and LHSV of 2.0. Reaction temperature varied from 260 to 400° C. The shale oil properties are given in Table 7. Product properties after upgrading are summarized in Table 8.

TABLE 7

Properties of Paraho Shale Oil Sample

| | |
|---|---|
| Gravity, °API | 21.7 |
| Hydrogen, wt % | 11.49 |
| Nitrogen, wt % | 2.2 |
| Sulfur, wt % | 0.69 |
| Arsenic, ppmw | 37 |
| Iron, ppmw | 27 |
| Nickel, ppmw | 2.4 |
| Bromine Number | 45 |
| Avg. Molecular Weight | 307 |
| C=C bonds per molecule | 0.85 |
| Simulated Distillation | D2887 (° C.) |
| 5% | 239 |
| 30% | 373 |
| 50% | 432 |
| 70% | 491 |
| 95% | — |

TABLE 8

Guard Chamber Processing of Shale Oil - Product Properties

| Temperature (° C.) | Bromine No. | Iron (ppmw) | Nickel (ppmw) | Arsenic (wt. %) | Sulfur (ppmw) | Nitrogen (ppmw) |
|---|---|---|---|---|---|---|
| 260 | 0.7 | 3.5 | 1.95 | 5.3 | 0.63 | 1.98 |
| 290 | <0.1 | 2.6 | 1.85 | 4.2 | 0.57 | 1.89 |
| 315 | <0.1 | 2.0 | 1.61 | 3.1 | 0.48 | 1.78 |
| 370 | <0.1 | 0.2 | 1.3 | <0.1 | 0.25 | 1.40 |
| 400 | <0.1 | <0.1 | 0.1 | <0.1 | <0.1 | 1.18 |

The evaluation shows that the catalytic material of Example 17 is very active for olefin saturation, removal of iron and nickel, denitrogenation, and desulfurization. It is also very active for arsenic removal.

EXAMPLE 27

Selective lube hydrocracking is preformed on a Ni- and W-containing mesoporous material of Example 18 above. The feedstock consists of a heavy neutral distillate having the properties given in Table 9 below, together with the properties of the oil after solvent dewaxing to −18° C. pour point (ASTM D-97 or equivalent such as Autopour). After solvent dewaxing, the nitrogen content is 1500 ppm; and the distillate viscosity index ("VI") is 53. In lube hydrocracking, the objective is to increase the unconverted material's VI level to the 95–100 range while maximizing lube yield.

TABLE 9

Heavy Neutral Distillate Properties

| | |
|---|---|
| Hydrogen, wt % | 12.83 |
| Nitrogen, ppm | 1500 |
| Basic Nitrogen, ppm | 466 |
| Sulfur, wt % | 0.72 |
| API Gravity | 22.0 |
| KV @ 100° C., cSt | 18.52 |
| Composition, wt % | |
| Paraffins | 18.3 |
| Naphthenes | 32.2 |
| Aromatics | 49.5 |
| Simulated Distillation, wt % | °C. |
| IBP | 405 |
| 5% | 452 |
| 10% | 471 |
| 95% | 586 |
| Solvent Dewaxed Oil Properties | |
| KV @ 100° C., cSt | 20.1 |
| Viscosity Index (VI) | 53 |
| Pour Point, ° C. | 0 |
| Lube Yield, wt % | 87 |

The distillate is processed at temperatures from 385 to 401° C., 138 bar hydrogen pressure, hydrogen circulation of 7500 SCF/B feed and 0.55, to 0.61 LHSV. The data from these experimental runs are summarized in Table 10 below:

TABLE 10

| | | | |
|---|---|---|---|
| Temp., ° C. | 125 | 739 | 754 |
| Pressure, bar | 138 | 138 | 138 |
| LHSV | 0.61 | 0.54 | 0.55 |
| 343 ° C.+ conv., wt % | 22.9 | 37.6 | 47.3 |
| Lube Properties | | | |
| KV @ 100° C., cSt | 11.05 | 7.89 | 5.45 |
| SUS @ 100° F. | 695 | 398 | 201 |
| VI | 86.2 | 110.2 | 126.3 |
| Pour Point, ° C. | 13 | 28 | 29 |
| Lube Yield, wt % | 71.5 | 60.6 | 51.3 |

The catalytic material is selective for upgrading the heavy neutral distillate from a raw distillate VI of 53 to a 105 VI product at a (undewaxed) lube yield of 65 wt %.

EXAMPLE 28

This example demonstrates the preparation of FCC catalyst using the composition of this invention and compares its cracking results with that of a catalyst using MCM-41. Catalyst preparation was as follows:

About 35 wt % of the composition of Example 4 in a silica-alumina-clay matrix was prepared. 130 parts of the composition of Example 4 were ball-milled for 14 hours in 230 ml $H_2O$. The product was rinsed from the mill with 52.5 ml of $H_2O$. A slurry was prepared containing 827 g of $H_2O$, 33.5 parts of kaolin clay (Georgia Kaolin Kaopaque), and 175.4 parts of hydrous silica (Philadelphia Quartz N-brand). The slurry was stirred and 16.4 parts of $H_2SO_4$ (96.7%) were added over a 30 minute period. 22.9 Parts of $Al_2(SO_4)_3 \cdot 16H_2O$ dissolved in 92.2 of $H_2O$ were added dropwise. 396 Parts of the ball-milled MCM-41 slurry (11.36% solids) were added to the silica-alumina-clay slurry, and the mixture was vigorously stirred at 800 rpm for 30 minutes and then filtered.

The solid was re-slurried in $H_2O$ and spray dried. The spray-dried product was slurried with $H_2O$ and the fines floating on the slurry were discarded. The remaining solid was exchanged with 1N $NH_4NO_3$ (5 cc $NH_4NO_3$/g of solid). The solid was washed with $H_2O$, filtered, and dried in an oven at 120° C.

A 50 g sample of this material was calcined at 540° C. for one hour in $N_2$ and 6 hours in air. The remainder of the oven-dried solid was steamed in 45% $H_2O$ at 650° C. for 4 hours. Prior to admitting steam to the reactor, the sample was heated to 650° C. in $N_2$. Air was gradually increased over a ½ hour period while the $N_2$ flow rate was increased. After the ½ hour period steam was admitted for the 4-hour period.

For comparison, a FCC catalyst containing 35 wt % MCM-41 was prepared in the same way as described above. The original MCM-41 had a surface area of 980 $m^2/g$, a pore size distribution centered around 2.5 nm, and a pore volume of 0.72 $cm^3/g$. It contained 5.4 wt % $Al_2O_3$, similar to 5.3 wt. % in the material of Example 4. Properties of the steamed catalysts are shown in Table 11.

TABLE 11

Comparison of the FCC catalyst containing the composition of the invention and the one containing MCM-41 after steaming.

| Catalyst | Invention Composition | MCM-41 |
|---|---|---|
| $SiO_2$, wt % | 72.6 | 71.8 |
| $Al_2O_3$, wt % | 13.8 | 13.7 |
| Surface area, $m^2/g$ | 462 | 307 |
| Avg. particle size, μm | 86 | 92 |
| Packed density, g/cc | 0.65 | 0.43 |

Catalytic Cracking Test

The two catalysts in Table 11 are evaluated for cracking Joliet Sour Heavy Gas Oil ("JSHGO") in a fixed-fluidized bed unit at 516° C. and one minute on stream. The JSHGO used had the properties shown in Table 12. The catalyst-to-oil ratio is varied from 2.0 to 6.0 to examine a wide range of conversions. The yields are summarized in Table 13, given on a constant coke (4.0 wt %) basis.

TABLE 12

Properties of JSHGO sample

| | |
|---|---|
| Density, g/cc | 0.8918 |
| Aniline Pt., ° C. | 80.8 |
| Hydrogen, wt % | 12.13 |
| Sulfur, wt % | 2.4 |
| Nitrogen, wt % | 0.41 |
| Basic Nitrogen, ppm | 382 |
| Conradson Carbon, wt % | 0.54 |
| KV 100° C., cSt | 8.50 |
| KV 40° C., cSt | N/A |
| Bromine No. | 8.7 |
| R.I. 21° C. | 1.496 |
| Pour Point, ° C. | 90 |
| Ni, ppm | 0.34 |
| V, ppm | 0.39 |
| Na, ppm | 1.3 |
| Fe, ppm | 0.3 |

Distillation Profile

| % Vol Distilled | T ° C. |
|---|---|
| 5 | 314 |
| 10 | 346 |
| 20 | 381 |
| 30 | 407 |
| 40 | 428 |
| 50 | 448 |

TABLE 12-continued

| | |
|---|---|
| 60 | 468 |
| 70 | 489 |
| 80 | 514 |
| 90 | 547 |
| 100 | 601 |
| % unrecovered | 0 |

TABLE 13

Catalytic cracking comparison between the catalyst containing the inventive composition and one containing MCM-41.

| Catalyst | The invention | MCM-41 | DELTA |
|---|---|---|---|
| Coke, wt % | 4.0 | 4.0 | |
| Conversion, wt % | 59.9 | 56.8 | 3.1 |
| $C_5$ + gasoline, wt % | 39.7 | 37.2 | 2.5 |
| RON | 93 | 92 | 1 |
| LFO, wt % | 31.5 | 32.2 | −0.7 |
| HFO, wt % | 10.2 | 11.0 | −0.8 |
| $C_4$'s, vol % | 14.7 | 13.3 | 1.4 |
| Light gas, wt % | 6.9 | 7.3 | −0.4 |
| $H_2$, wt % | 0.03 | 0.04 | −0.01 |
| $C_5$'s, vol % | 5.5 | 4.7 | 0.8 |

EXAMPLE 29

A medium pressure hydrocracked bottoms fraction was subjected to catalytic dewaxing and hydroprocessing. The feed was processed in cascade operation over fixed bed reactors. Eighty grams of HZSM-5 dewaxing catalyst was loaded into a first reactor and 240 g of the invention catalyst as described in Example 19 was loaded into the second reactor. The feed is passed over both catalysts at 175 bar, 1.0 LHSV over the dewaxing catalyst, 0.33 LHSV over the hydroprocessing catalyst. The temperature in the first reactor was maintained at 307–321° C. to give a target pour point of −6.6° C. The properties of the bottoms fraction are described below in Table 14.

TABLE 14

Heaviest 10% of Bottoms Properties at 45 wt. % 377° C.+ conversion

| | |
|---|---|
| Nitrogen, ppm | 9 |
| Mol. Weight | 558 |
| Pour Point, ° C. | >120 |
| KV @ 100° C., cSt | 11.3 |
| Composition, wt % | |
| Paraffins | 42.1 |
| Mononaphthenes | 19.9 |
| Polynaphthenes | 21.2 |
| Aromatics | 16.8 |
| Simulated Distillation | ° F. |
| IBP/5 | 209/854 |
| 10/50 | 902/982 |

UV absorbance of the product was used to determine the aromatics in the lubricant base stock. The absorbance at 226 nm is a measure of the total aromatics while the absorbance at 400 nm ($\times 10^3$) is a measure of the polynuclear aromatics. For comparative purposes over Pd/MCM-41, catalysts prepared in accordance with the procedure described in Example 19 were also tested. The results of the runs are summarized in the following Table 15.

TABLE 15

Lube Hydrotreating at 274° C.

| Run | 1 | 2 |
|---|---|---|
| Metal | Pd | Pd |
| Support | MCM-41 | Example 1 |
| Total aromatics, 226 nm | 0.210 | 0.120 |
| Polynuclear aromatics, 400 nm ($\times 10^3$) | 1.30 | 0.78 |

Comparing the performance of the Pd/MCM-41 catalyst with the catalyst containing Pd on the composition of this invention, it is apparent that the composition of this invention is much more effective in saturating aromatics.

EXAMPLE 30

This example demonstrates using the composition of the invention as a catalyst for hydrotreating of a coal liquid. While the specific coal-derived liquid exemplified here is a liquefaction product of the H-Coal process (using Illinois No. 6 coal as the starting material), other coal liquids (e.g. coal tar extracts, solvent refined coal, etc.) can be similarly upgraded. The catalyst sample was made in the same way as described in Example 3A. However, the method included hydrothermal treatment in an autoclave at 190° C. for a relatively short period of time of 4 days. Nitrogen adsorption showed mesopores with a size centered at 11 nm with a surface area of about 630 $m^2$/g. Elemental analysis showed a Si/Al atomic ratio of about 99.6.

The material is further impregnated with an ammonium heptamolybdate solution. Particularly, 45.12 parts of an aqueous solution containing 6.38 parts of ammonium heptamolybdate is added to 40 parts of the above material. The resulting wet material was dried at 120° C. and calcined in air at 538° C. under conditions sufficient to decompose ammonium heptamolybdate and generate $MoO_3$, thereby producing a molybdenum impregnated material.

The molybdenum-impregnated material is then impregnated with a nickel nitrate solution. Particularly, 48.2 parts of an aqueous solution containing 9.3 parts of $Ni(NO_3)_2 \cdot 6H_2O$ is added to the molybdenum-impregnated material. The resulting wet material is dried at 121° C. and then calcined in air at 538° C. to decompose nickel nitrate and generate NiO, thereby producing a nickel and molybdenum impregnated material. Elemental analysis shows that the final material contains 15.0 wt % of $MoO_3$ and 6.4 wt % of NiO.

For comparison, an MCM-41 material is used, which has a surface area of 992 $m^2$/g, a pore size distribution centered at 3.5 nm, and a pore volume of 0.72 $cm^3$/g. It is impregnated in the same way as described above and finally contains 15.2 wt % of $MoO_3$ and 6.7 wt % of NiO.

Their activities for hydrotreating are evaluated using Illinois H-coal as feedstock. Table 16 shows the properties of the feedstock.

TABLE 16

(Properties of Illinois H-coal)

| | |
|---|---|
| Gravity, °API | 25.8 |
| Aniline Point ° C. | <−1.1 |
| Molecular Weight | 147 |
| Viscosity, cSt at 38° C. | 1.645 |
| CCR, Wt. % | 0.29 |
| Bromine No. | 42 |

TABLE 16-continued (Properties of Illinois H-coal)

| Carbon, Wt. % | 86.96 |
|---|---|
| Hydrogen, Wt. % | 11.39 |
| Sulfur, Wt. % | 0.32 |
| Oxygen, Wt. % | 1.80 |
| Total Nitrogen, Wt. % | 0.46 |
| Basic Nitrogen, Wt. % | 0.30 |
| Iron, ppm | 22 |
| Chloride, ppm | 32 |
| TRP Distillation, ° C. | |
| St/5 | 13/81 |
| 10/30 | 101/167 |
| 50 | 207 |
| 70/90 | 242/309 |
| 95/99 | 346/407 |

These two catalysts are presulfided for a period of 1 hour in a 500 cm$^3$/min flow of 10% H$_2$S in H$_2$ at 230° C. and a total pressure of 680 kPa. Hydrotreating is conducted at a temperature of 350° C., a pressure of 6890 kPa, a hydrogen flow rate of 500 cm$^3$/min, a liquid hour space velocity of 0.33. Table 17 shows the comparison of activity in terms of denitrogenation, Conradson Carbon Residue (CCR) reduction, and desulfurization.

TABLE 17

Comparison of hydrotreating activity

| Catalyst | This invention | MCM-41 catalyst |
|---|---|---|
| Denitrogenation (%) | 73 | 48 |
| CCR reduction (%) | 98 | 63 |
| Desulfurization (%) | 95 | 58 |

The catalyst of this invention shows much higher activity, which partially should be attributed to its unique pore structure. It has relatively large pores with three-dimensional connection, which can accommodate and transport large molecules such as present in coal liquids.

EXAMPLE 31

This Example demonstrates the preparation of Fischer-Tropsch catalyst and its catalytic performance. Twenty (20) parts of Al-containing material made in Example 1 is dried at 200° C. for half an hour under N$_2$ flow. It is then mixed thoroughly with 2 parts of Co$_2$(CO)$_8$ in a glove box. This mixture of solids is placed into a tube furnace boat in a sealed tube and removed from the glove box. Then it is heated in flowing helium at 100° C. for 15 minutes, raised to 200° C. over 10 minutes, then heated at 200° C. in helium for half an hour. The final catalyst contains 16 wt. % Co.

The above catalyst is treated with hydrogen prior to test. It is placed in a small quartz crucible in a chamber and purged with nitrogen at 8.5×10$^{-6}$ Nm$^3$/s at room temperature for 15 minutes. It is then heated at 1° C./min to 100° C. under flowing hydrogen at 1.8×10$^{-6}$ Nm$^3$/s and held at 100° C. for one hour. It is then heated at 1° C./min to 400° C. and held at 400° C. for four hours under flowing hydrogen at 1.8×10$^{-6}$ Nm$^3$/s. The catalyst is cooled in hydrogen and purged with nitrogen before use.

A pressure vessel containing the catalyst and n-octane is heated at 225° C. under 69 bar of H$_2$; CO (2:1) and held at that temperature and pressure for 1 hour. The reactor vessel is cooled in ice, vented, and an internal standard of di-n-butylether is added. Hydrocarbons in the range of C$_{11}$–C$_{40}$ are analyzed relative to the internal standard by GC.

A C$_{11}^+$ Productivity (g C$_{11}^+$/hour/kg catalyst) is calculated to be 234 based on the integrated production of the C$_{11}$–C$_{40}$ hydrocarbons per kg of catalyst per hour. The logarithm of the weight fraction for each carbon number ln(Wn/n) is plotted as the ordinate vs. number of carbon atoms in (Wn/n) as the abscissa. From the slope, a value of alpha is obtained to be 0.87.

While the above description contains many specifics, these specifics should not be construed as limitations on the scope of the invention, but merely as exemplifications of preferred embodiments thereof. Those skilled in the art will envision many other possibilities within the scope and spirit of the invention as defined by the claims appended hereto.

What is claimed is:

1. A process for treating organic compounds which comprises:
    a) providing a composition which includes a substantially mesoporous structure of silica containing at least 97% by volume of pores having a pore size ranging from about 15 Å to about 300 Å and having a micropore volume of at least about 0.01 cc/g, and wherein the mesoporous structure has incorporated therewith at least about 0.02% by weight of at least one catalytically and/or chemically active heteroatom selected from the group consisting of Al, Ti, V, Cr, Zn, Fe, Sn, Mo, Ga, Ni, Co, In, Zr, Mn, Cu, Mg, Pd, Ru, Pt, W and combinations thereof, said composition has an X-ray diffraction pattern with one peak at 0.3° to about 3.5° at 2 θ;
    b) contacting an organic compound-containing feed under reaction conditions with said composition wherein the treating process is selected from the group consisting of alkylation, acylation, oligomerization, selective oxidation, hydrotreating, isomerization, catalytic dewaxing, hydroxylation, hydrogenation, ammoximation, dehydrogenation, cracking and adsorption.

2. The process of claim 1 wherein the treating process is alkylation, and wherein the organic compound-containing feed comprises an aromatic compound or alkane and an alkylation agent.

3. The process of claim 2 wherein the aromatic compound is selected from the group consisting of benzene, naphthalene, phenanthrene, toluene, xylene, isopropylnaphthalene, diphenyloxide, and 2,4-di-tert-butylphenol.

4. The process of claim 3 wherein the alkylation agent is an olefin or an alcohol.

5. The process of claim 4 wherein the at least one heteroatom is Al and/or Ga.

6. The process of claim 5 wherein the aromatic compound is naphthalene or benzene and the olefin is 1-hexadecene or ethylene.

7. The process of claim 3 wherein the alkylation agent is an organic halide, and wherein the at least one heteroatom is selected from the group consisting of Sn, Ga, Fe and combinations thereof.

8. The process of claim 7 wherein the aromatic compound is benzene and the organic halide is chlorobenzene.

9. The process of claim 1 wherein the treating process is selective oxidation, the feed includes an oxidizing agent and the at least one heteroatom is selected from the group consisting of Cu, Zn, Fe, Ti, V, Sn, Mn, Cr, Mo and combinations thereof.

10. The process of claim 9 wherein the at least one heteroatom includes at least one atom selected from the group consisting of Ti, Cr and Mo, the feed includes ethylbenzene, and wherein a product of the selective oxidation treating process includes acetophenone.

11. The process of claim 9 wherein the feed includes an alcohol and the at least one heteroatom includes Cu and/or Zn.

12. The process of claim 9 the organic feed includes cyclohexanol and a product of the selective oxidation treating process includes cyclohexanone.

13. The process of claim 1 wherein the treating process is oligomerization, the feed comprises at least one olefin, and the at least one heteroatom is selected from the group consisting of Al, Cr, Ga, Fe and combinations thereof.

14. The process of claim 13 wherein the organic feed includes 1-decene and the at least one heteroatom includes Al.

15. The process of claim 1 wherein the treating process is acylation, the feed contains at least one aromatic compound and at least one acylation agent, and the at least one heteroatom is selected from the group consisting of Al, Fe, Ga, In and combinations thereof.

16. The process of claim 15 wherein the feed includes 2-methoxynaphthalene and acetic anhydride.

17. The process of claim 1 wherein the treating process includes hydrotreating and the at least one heteroatom is selected from the group consisting of Ni, Mo, Co, W, Pt, Pd and combinations thereof.

18. The process of claim 17 wherein the organic feed includes shale oil, or derived coal liquid, or residual petroleum fractions, the hydrotreating includes one or more of denitrogenation, desulfurization, CCR reduction and demetalation.

19. The process of claim 18 wherein the demetalation includes the removal of iron, nickel, vanadium and arsenic.

20. The process of claim 19 wherein the feed is a petroleum residuum, the hydrotreating includes one or more of denitrogenation, desulfurization, demetalation, and CCR reduction.

21. The process of claim 1 wherein the treating process includes cracking.

22. The process of claim 21 wherein the cracking is hydrocracking and the at least one heteroatom includes one or more metals selected from the group consisting of Ni, W, Mo, Co, Al and Ga.

23. The process of claim 20 wherein the cracking is catalytic cracking and the at least one heteroatom includes Al.

24. The process of claim 1 wherein the treating process is catalytic dewaxing and the at least one heteroatom includes at least one atom selected from the group consisting of Al, Pt and Pd.

25. The process of claim 1 wherein the treating process is hydroxylation, the at least one heteroatom is selected from the group consisting of Ti, Fe, Cu, Co, V, Cr and combinations thereof.

26. The process of claim 25 wherein the feed contains phenol and/or naphthol.

27. The process of claim 1 wherein the treating process is isomerization and the at least one heteroatom is selected from the group consisting of Pd, Pt, Ni, Zr, W, Ga, Fe, Ti, Al and combinations thereof.

28. The process of claim 27 wherein the feed includes at least one hydrocarbon selected from the group consisting of n-butane, n-pentane, 1-butene, xylene and a waxy petroleum stream with an average carbon number more than 20.

29. The process of claim 1 wherein the treating process is dehydrogenation and the at least one heteroatom is selected from the group consisting of Zn, W, Ga, Fe, Ti, Al, Sn and combinations thereof.

30. The process of claim 29 wherein the feed includes one or more saturated hydrocarbons.

31. The process of claim 30 wherein the saturated hydrocarbons are selected from the group consisting of n-butane, n-pentane, 1-butene and xylene.

32. The process of claim 1 wherein the treating process is Fischer-Tropsch and the at least one heteroatom is selected from the group consisting of Fe, Co, Ni and Ru and combinations thereof.

33. The process of claim 1 wherein the composition contact with a feed contain hydrogen and carbon monoxide under conditions: a pressure from of about 5 bar to about 60 bar, a GHSV from about 100 $hr^{-1}$ to about 10,000 $hr^{-1}$, a temperature from about 160° C. to about 300° C.

34. The process of claim 1 wherein the composition further includes a zeolite.

* * * * *